United States Patent
Rothenberg et al.

(10) Patent No.: US 10,294,517 B2
(45) Date of Patent: May 21, 2019

(54) GENETIC TEST FOR DETERMINING SUSCEPTIBILITY FOR EOSINOPHILIC ESOPHAGITIS

(71) Applicant: CHILDREN'S HOSPITAL MEDICAL CENTER, Cincinnati, OH (US)

(72) Inventors: Marc E. Rothenberg, Cincinnati, OH (US); Leah Kottyan, Blue Ash, OH (US); John Harley, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 219 days.

(21) Appl. No.: 15/127,328

(22) PCT Filed: Mar. 16, 2015

(86) PCT No.: PCT/US2015/020768
§ 371 (c)(1),
(2) Date: Sep. 19, 2016

(87) PCT Pub. No.: WO2015/142739
PCT Pub. Date: Sep. 24, 2015

(65) Prior Publication Data
US 2017/0183719 A1    Jun. 29, 2017

Related U.S. Application Data

(60) Provisional application No. 61/954,411, filed on Mar. 17, 2014.

(51) Int. Cl.
*C12Q 1/68* (2018.01)
*C12P 19/34* (2006.01)
*C12Q 1/6827* (2018.01)
*C12Q 1/6883* (2018.01)

(52) U.S. Cl.
CPC ......... *C12Q 1/6827* (2013.01); *C12Q 1/6883* (2013.01); *C12Q 2600/156* (2013.01)

(58) Field of Classification Search
None
See application file for complete search history.

(56) References Cited

PUBLICATIONS

"rs77569859", Dec. 16, 2010 (Dec. 16, 2010), pp. 1-2, Retrived from the Internet: URL: http://www.ncbi.nlm.nih.gov/projects/SNP/snp-SS.cgi?subsnp_id=276404309.
"rs2898261", Dec. 16, 2010 (Dec. 16, 2010), pp. 1-2, Retrieved from the Internatnet: URL:http://www.ncbi.nlm.nih.gov/projects/SNP/snp_ss.cgi?subsnp_id=279682708.
"rs8041227", Feb. 26, 2008 (Feb. 26, 2008), pp. 1-3, Retrieved from the Internet: URL:http//www.ncbi.nlm.nih.gov/prjects/SNP/snp_ss.cgi?subsnp_id=90109558.
Joseph D. Sherrll et al: "Variants of thymic stromal lymphopoietin and its receptor associate with eosinophilic esophagitis", Journal of Allergy and Clinical Immunology, vol. 126, No. 1, Jul. 1, 2010 (Jul. 1, 2010), pp. 160-165.e3.
Leah C. Kottyan et al: "genome-wide association analysis of eosinophilic esophagitis provides insight into the tissue specificity of this allergic disease", Nature Genetics, vol. 46, No. 8, Jul. 13, 2014 (Jul. 13, 2014), pp. 895-900.
International search report issued in PCT/US2015/020768 on Jun. 12, 2015.

*Primary Examiner* — Young J Kim
(74) *Attorney, Agent, or Firm* — Muriel Liberto, Esq.; Mintz Levin Cohn Ferris Glovsky and Popeo, P.C.

(57) ABSTRACT

Methods and compositions disclosed herein generally relate to determination of susceptibility to eosinophilic esophagitis, asthma, and/or allergic diseases, disorders, and/or pulmonary and/or upper gastrointestinal conditions arising therefrom and/or related thereto and the diagnosis, treatment, and/or management of eosinophilic esophagitis, asthma, and/or allergic diseases, disorders, and/or pulmonary and/or upper gastrointestinal conditions arising therefrom and/or related thereto. Embodiments of the invention relate to the association between genes and specific polymorphisms of genes with eosinophilic esophagitis. Embodiments of the invention can be used to determine and manage patient risk factors for development of eosinophilic esophagitis; this determination can then be used to diagnose eosinophilic esophagitis and to treat a patient diagnosed with eosinophilic esophagitis.

10 Claims, 24 Drawing Sheets

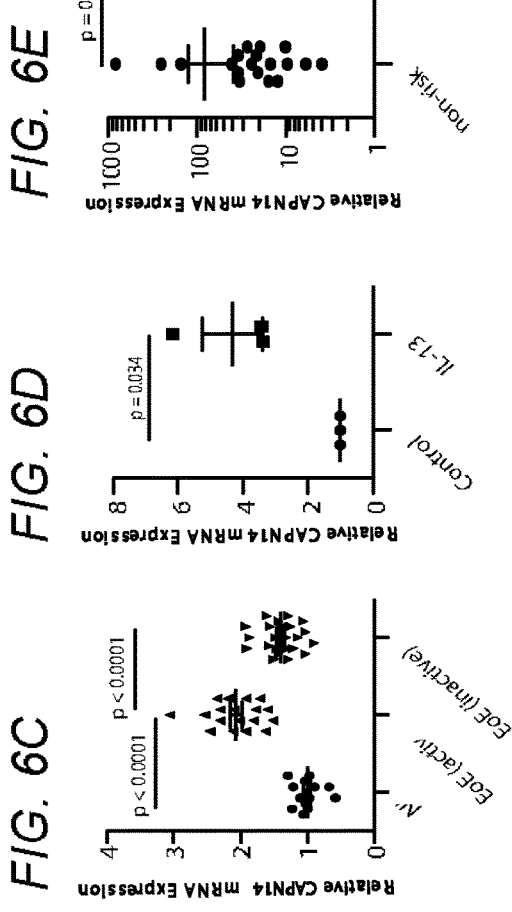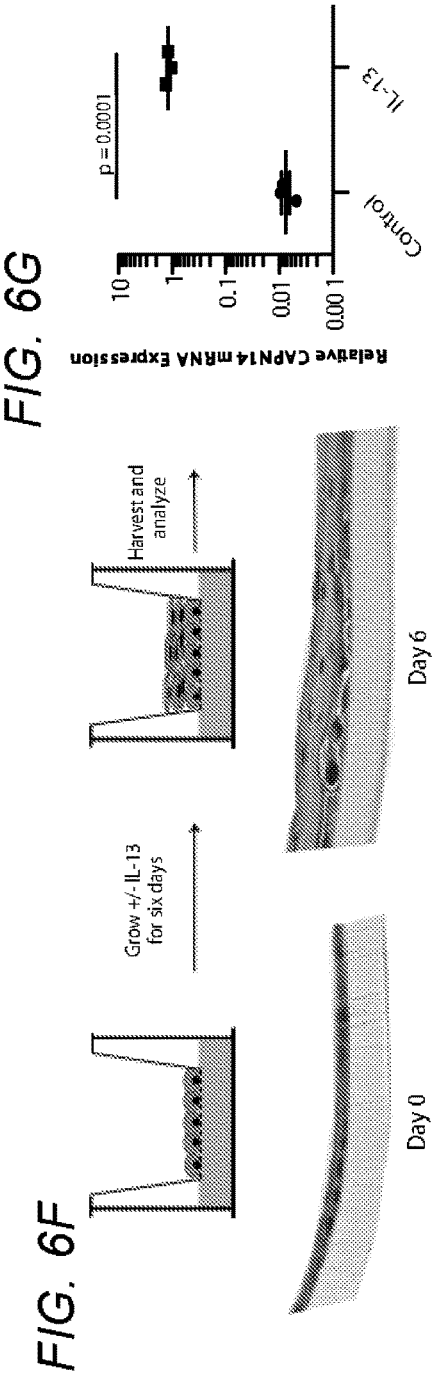

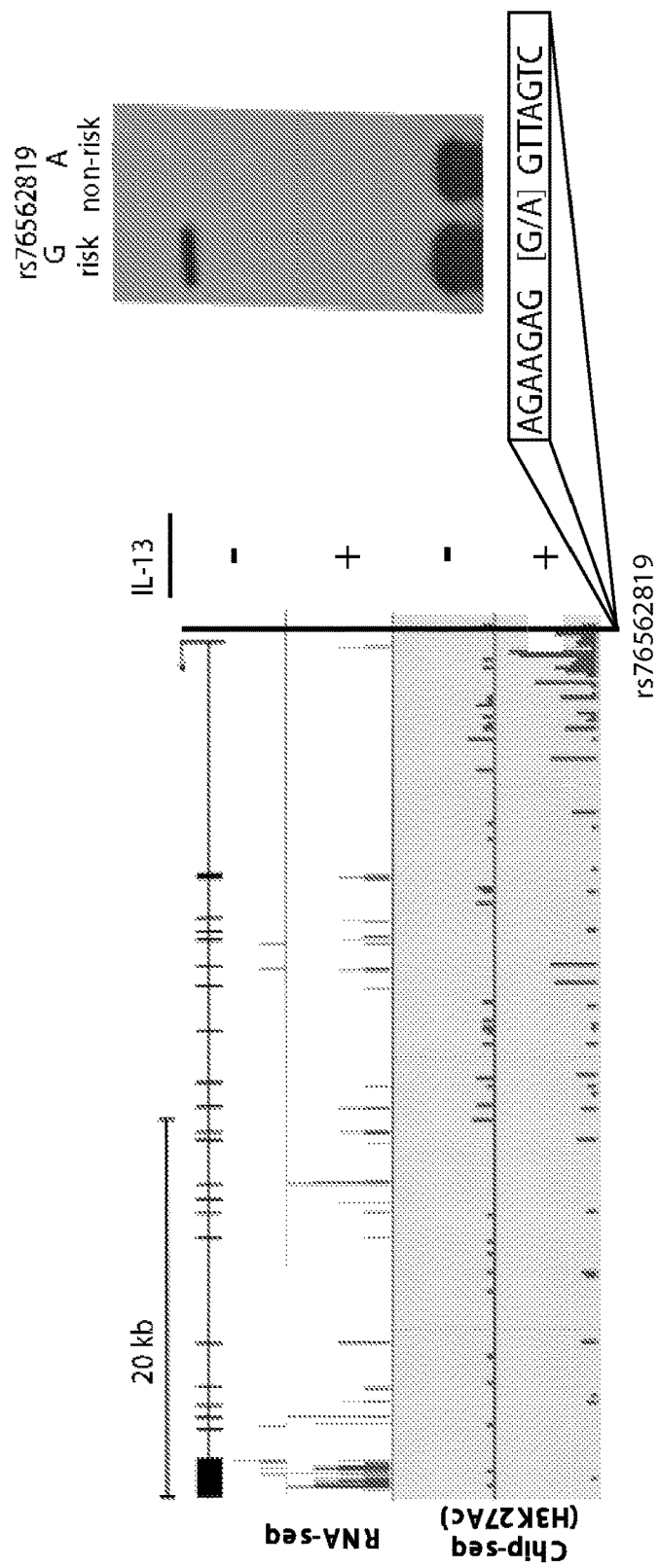

|  | Fold change | H3K27Ac M value | p-value |
|---|---|---|---|
| CAPN14 | 6.02 | -3.08 | $5.8 \times 10^{-5}$ |
| RARB | 5.19 | -1.5 | 0.0001 |

*FIG. 13A*  CLEC16A
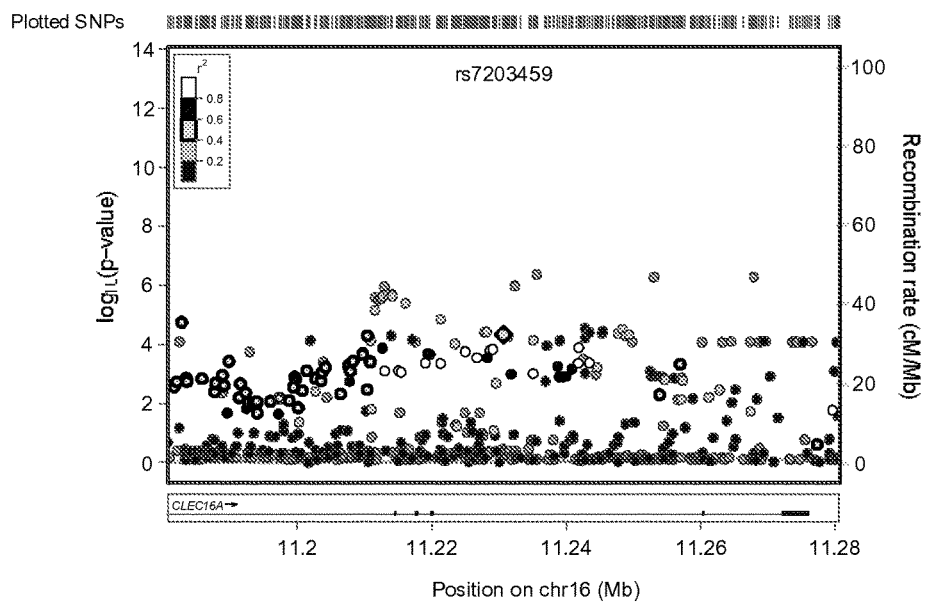
*FIG. 13B*  C11orf30/LRR32
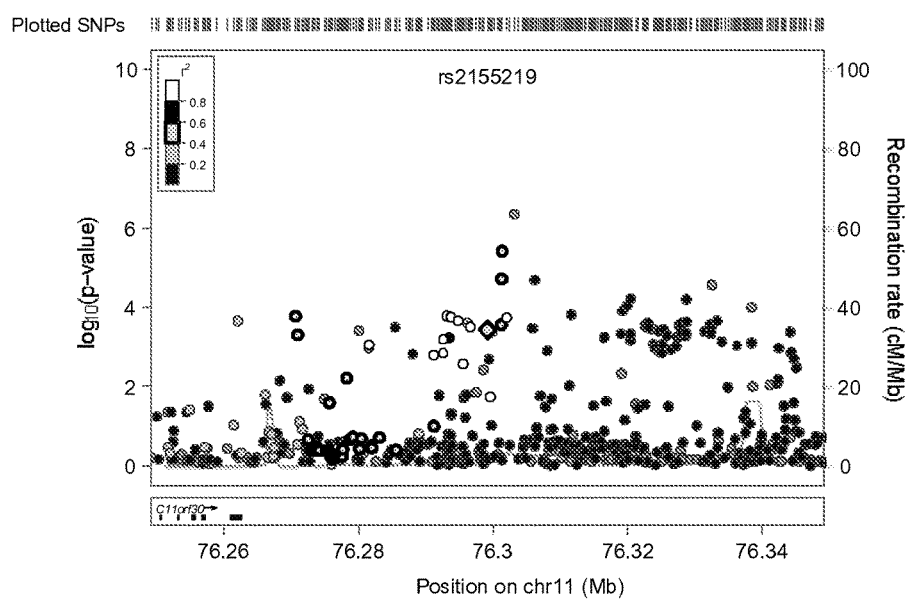

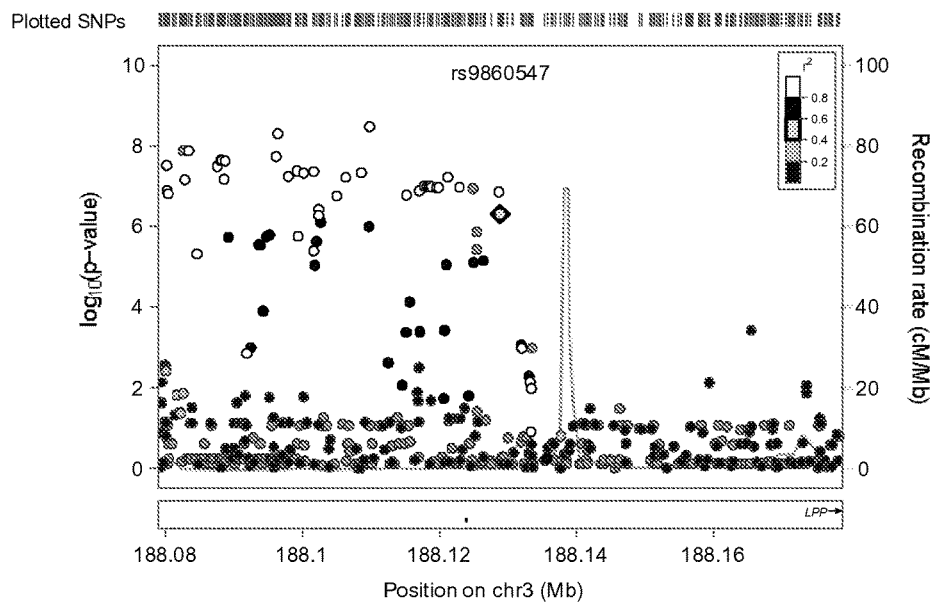
FIG. 13C  LPP
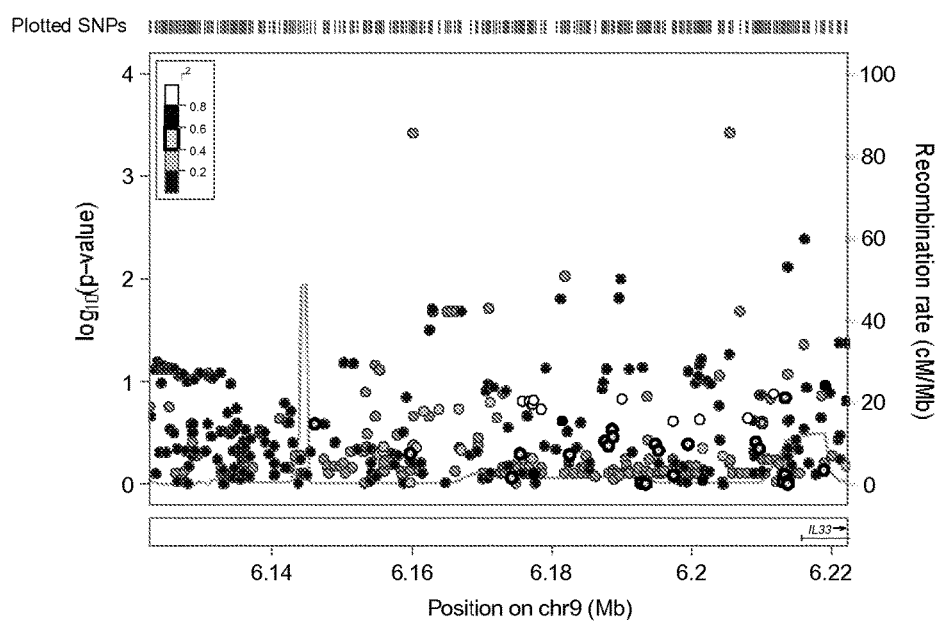
FIG. 13D  IL-33

US 10,294,517 B2

GENETIC TEST FOR DETERMINING SUSCEPTIBILITY FOR EOSINOPHILIC ESOPHAGITIS

CROSS-REFERENCES TO RELATED APPLICATIONS

This application is a national stage entry, filed under 35 U.S.C. § 371, of International Application No. PCT/US2015/020768, filed on Mar. 16, 2015, and claims the benefit of and priority to U.S. Provisional Patent Application No. 61/954,411, filed Mar. 17, 2014, the entire contents of which is hereby incorporated herein by reference in its entirety and for all purposes.

STATEMENT REGARDING FEDERALLY-SPONSORED RESEARCH

This invention was made with government support under AI066738 and HL007752 awarded by the National Institutes of Health. The government has certain rights in the invention.

FIELD OF THE INVENTION

The invention disclosed herein generally relates to determination of susceptibility to eosinophilic esophagitis, asthma, and/or allergic diseases, disorders, and/or pulmonary and/or upper gastrointestinal conditions arising therefrom and/or related thereto and the diagnosis, treatment, and/or management of eosinophilic esophagitis, asthma, and/or allergic diseases, disorders, and/or pulmonary and/or upper gastrointestinal conditions arising therefrom and/or related thereto.

BACKGROUND

All publications mentioned herein are incorporated by reference to the same extent as if each individual publication or patent application was specifically and individually indicated to be incorporated by reference. The following description includes information that can be useful in understanding the present subject matter. It is not an admission that any of the information provided herein is prior art or relevant to the presently claimed subject matter, or that any publication specifically or implicitly referenced is prior art.

Eosinophilic esophagitis (EoE) is a chronic, food antigen-driven, tissue-specific esophageal, inflammatory disease of the esophagus. EoE is characterized by marked mucosal eosinophil accumulation that is often associated with fibrosis, stricture formation, and impaired motility (Liacouras, C. A. et al., *J Allergy Clin Immunol* 128:3-20 e6, quiz 21-2 (2011); Rothenberg, M. E. *Gastroenterology* 137:1238-49 (2009); Collins, M. H. et al. *Clin Gastroenterol Hepatol* 6:621-9 (2008); Putnam, P. E. and Rothenberg, M. E. *Curr Gastroenterol Rep* 11:220-5 (2009)).

Allergens are thought to drive EoE pathogenesis. This is because the disease remits after removal of specific food types, reoccurs upon food re-introduction, is associated with marked dysregulation of esophageal transcripts rich in elements involved in allergic inflammation (e.g. T helper cell type 2 (Th2) cytokines such as interleukin (IL)-13, eosinophils, and mast cells), and can be induced in mice by allergen exposure through IL-5- and IL-13-driven pathways (Abonia, J. P. and Rothenberg, M. E. *Annu Rev Med* 63:421-34 (2012); Davis, B. P. and Rothenberg, M. E. *Expert Rev Clin Immunol* 9:285-7 (2013); Henderson, C. J. et al. *J Allergy Clin Immunol* 129:1570-8 (2012); Rothenberg, M. E. et al. *J Allergy Clin Immunol* 130:617-9 (2012)).

SUMMARY OF THE INVENTION

The invention provides methods for identifying a patient as having or at risk of developing eosinophilic esophagitis (EoE) and related diagnostic methods and bioassay kits, the methods comprising assaying for at least one genetic variant determined by the inventors to be associated with EoE, as described in detail infra. The invention also provides related computer implemented methods and systems.

In one aspect, the present invention provides methods for identifying a patient as having or at risk of developing eosinophilic esophagitis (EoE), the method comprising determining or receiving the patient's genotype for one or more genetic variants selected from the group consisting of rs77569859 (CAPN14), rs2898261 (XKR6), and rs8041227 (located at 15q13 between LOC283710 and KLF13), assigning the patient into a risk group selected from low, moderate, and high, based upon patient specific data including at least the patient's genotype at the one or more genetic variants, such that a patient assigned to the high risk group is identified as a patient having or at risk of developing EoE. Such patients should, in general, be referred for a further confirmatory diagnostic test, such as endoscopy.

The term, "at risk of developing" EoE in the context of the present methods refers to an increased risk relative to the risk of EoE in the general population or relative to the risk for an individual not carrying the genetic variant identified herein as associated with a "high" risk of EoE. Patients assigned to a low risk group, based at least on the patient's genotype for at least one of the genetic variants described herein, are not believed to be at an increased risk of EoE and may be identified or classified, for example, as "low risk" of EoE. These patients, generally, should not be referred for a further diagnostic test, such as endoscopy. Patients assigned to a moderate risk group may have an increased risk of developing EoE and such patients may, for example, be monitored for additional signs and symptoms of EoE. In some circumstances, patients in the moderate risk group may have other patient-specific factors that are also associated with an increased risk of EoE. In such circumstances, patients in the moderate risk group may be referred for a further confirmatory diagnostic test, such as endoscopy.

The invention also provides related diagnostic tests and methods for determining a patient's susceptibility to eosinophilic esophagitis (EoE). The diagnostic test may comprise, for example, a bioassay kit as described infra. The diagnostic method comprises determining or receiving the patient's genotype for the one or more genetic variants described above and assigning the patient into a risk group as described above, such that a patient assigned to the high or moderate risk group is determined to be a patient who is susceptible to EoE, while a patient assigned to the low risk group is classified as not susceptible to EoE, meaning that the patient has no increased risk of EoE, as discussed above.

The invention also provides computer-implemented methods and systems for identifying a patient having or at risk of developing EoE, and for diagnosing a patient's susceptibility to EoE, the methods comprising determining or receiving, by at least one data processor, the patient's genotype for one or more genetic variants selected from the group consisting of rs77569859 (CAPN14), rs2898261 (XKR6), and rs8041227 (located at 15q13 between LOC283710 and KLF13), assigning the patient, by at least one data processor, into a risk group selected from low, moderate, and high, based upon patient specific data including at least the patient's genotype for the one or more genetic variants, wherein the patient assigned to the high risk group is identified as a patient having or at risk of developing EoE.

The invention also provides a system for identifying a patient having or at risk of developing EoE, the system comprising a database for storing the patient's genotype for one or more genetic variants selected from the group consisting of rs77569859 (CAPN14), rs2898261 (XKR6), and rs8041227 (located at 15q13 between LOC283710 and KLF13), and risk groups designated low, moderate, and high; and a processor configured to assign the patient into one of the risk groups based upon patient specific data including at least the patient's genotype for the one or more genetic variants, wherein the patient assigned to the high risk group is identified as a patient having or at risk of developing EoE.

The methods and systems described herein may also comprise a further step of performing one or more additional diagnostic tests if the patient is identified as a patient having at risk of developing EoE, for example, if the patient is assigned to a high or moderate risk group based upon the patient's genotype for a variant described herein. In one embodiment, the one or more additional diagnostic tests comprises or consists of endoscopy.

In accordance with the methods and systems described herein, the step of assigning the patient into a risk group selected from low, moderate, and high, based upon the patient's genotype is performed by associating particular genotypes with risk of EoE as follows:

rs77569859 (CAPN14) GG high, GA moderate, AA low;
rs2898261 (XKR6) CC high, AC moderate, CC low; and
rs8041227 (15q13) GG high, AG moderate, AA low, Where the terms "high", "moderate", and "low", refer to the risk group to which the patient is assigned based upon the genotype indicated. Preferably, the assigning is performed by a computer implemented method. In one embodiment, the result of the assigning step, for example an indication of the risk group to which the patient is assigned, is displayed on a device suitable for displaying text or graphics, including a computer monitor or smart phone. In one embodiment, the computer implemented method comprises a decision rule or a machine learning algorithm, or both.

In accordance with the methods and systems described herein, the assigning the patient into a risk group may further be based upon patient specific data including at least one additional non-genetic factor. In one embodiment, the at least one additional non-genetic factor is selected from gender, race, age, and diagnosis.

In one embodiment, each genotype is assigned a numerical value between 0 and 1 based on its associated risk.

In one embodiment, the patient's genotype is received directly from equipment used in determining the patient's genotype.

The patient's genotype may be determined by any suitable method. In one embodiment, the patient's genotype is determined by a method comprising obtaining or receiving a biological sample from the patient, extracting DNA from the sample, and analyzing the DNA to determine the patient's genotype at the at least one genetic variant. In one embodiment, the DNA is analyzed using a polymerase chain reaction based genotyping platform. In one embodiment, the genotyping platform utilizes a 5' nuclease assay for amplifying and detecting specific genetic variants. In one embodiment, the biological sample is selected from a blood sample, a saliva sample, and a buccal swab.

The invention also provides a bioassay kit comprising the following components (i) a set of sequence-specific forward and reverse primers effective to amplify at least one of the following SNPs: rs77569859 (CAPN14), rs2898261 (XKR6), and rs8041227 (15q13); (ii) two labelled DNA probes, each effective to hybridize to a different allele of each SNP; and (iii) a DNA polymerase having 5' nuclease activity.

In one embodiment, the one or more genetic variants consists of rs77569859 (CAPN14).

In one embodiment, the one or more genetic variants consists of rs2898261 (XKR6).

In one embodiment, the one or more genetic variants consists of rs8041227 (located at 15q13 between LOC283710 and KLF13).

In one embodiment, the one or more genetic variants consists of all three variants, rs77569859 (CAPN14), rs2898261 (XKR6), and rs8041227 (located at 15q13 between LOC283710 and KLF13).

BRIEF DESCRIPTION OF THE DRAWINGS

Those of skill in the art will understand that the drawings, described below, are for illustrative purposes only. The drawings are not intended to limit the scope of the present teachings in any way.

FIG. 1. Manhattan plot of the p-values obtained from the genome-wide association analysis.

FIG. 2. Manhattan plot of the p-values obtained from the genome-wide association analysis.

FIG. 4. Genetic association of variants at the 5q22 locus with EoE risk comparison to the association pattern seen in genetic studies for other allergic diseases.

of the genetic association analysis are plotted as a function of genomic positions of each imputed variant (MAF>0.01) on chromosome 5 (Chr5) using a logistic regression, with the apparent association intervals of variants at 5q22 identified with black lines.

FIG. 6. CAPN14 is specifically expressed in the esophageal epithelium, dynamically upregulated as a function of disease activity and genetic haplotype, and after exposure of epithelial cells to IL-13. FIG. 6C. Microarray expression analysis of CAPN14 expression from esophageal biopsies. FIG. 6D. Microarray expression analysis of primary esophageal epithelial cells with or without IL-13 stimulation for 48 hours. Error bars represent standard error of the mean (s.e.m.). FIG. 6E. Real-time PCR analysis of CAPN14 expression in biopsies from EoE patients with the non-risk haplotype (n=19) or with at least one copy of the risk haplotype at the 2p23 loci (n=17). The risk haplotype is defined as having the EoE-risk allele at each of the six most highly associated variant locations. Error bars represent s.e.m. FIG. 6F. Schematic of esophageal epithelial air-liquid interface (ALI) transwell culture system and H&E staining demonstrating stratification. FIG. 6G. RNA-seq expression analysis of CAPN14 expression from ALI cultures with or without IL-13 stimulation for 6 days (n=3 for each group). Error bars represent s.e.m. FIG. 6H. Chip-seq on TE-7 cells shows increased H3K27Ac marks with IL-13 stimulation over the transcriptional start site of CAPN14, which correlates with an increase in transcriptional activity by RNA-seq. One significantly associated SNP (rs76562819) is in this acetylation region. FIG. 6I. Electrophoretic mobility shift assay (EMSA) was used to probe nuclear lysates from an esophageal epithelial cell line using oligonucleotides with the risk [G] or non-risk [A] allele of rs76562819.

FIG. 8. IL-13 induces CAPN14 expression and calpain activity.

FIG. 12. Proposed model of increased EoE risk at CAPN14 locus. CAPN14 is expressed specifically in the esophagus (FIG. 6A). Allergic inflammatory mediators including IL-13 and IL-4 induce CAPN14 expression and activity (FIG. 6H and FIG. 8A and (Ueta, M. et al. *Br J Ophthalmol* 94, 1239-43 (2010); Ueta, M. et al. *Jpn J Ophthalmol* 55:405-10 (2011))), and the regulation of the increased expression is mediated in part through the acetylation of histones (FIG. 6I). The abundance of IL-13 and IL-4 in the esophagus of patients with EoE (Marchini, J. et al. *Nat Genet* 39:906-13 (2007); Altshuler, D. M. et al. *Nature* 467:52-8 (2010); Zimmermann, N. et al. *J Clin Invest* 111:1863-74 (2003); Blanchard, C. et al. *J Clin Invest* 116:536-47 (2006)) results in increased CAPN14 expression (FIGS. 6B-D) and activity (FIG. 8B), and the calpain activity of CAPN14 potentially attenuates further inflammation by digesting endogenous proteins. The genetic variants associated with EoE risk at the CAPN14 locus lead to decreased CAPN14 expression (FIG. 6E) feasibly through the binding of a protein, a transcription factor that potentially acts as a transcriptional repressor.

FIG. 13. Association of variants in loci previously reported to be associated with allergic sensitization with EoE-risk. The variant that was most highly associated in the allergic sensitization study is indicated in each panel. The linkage disequilibrium (LD) values ($r^2$) between the lead SNP and the other SNPs as assessed in the March 2012 release of the 1,000 genomes project are indicated in different shades. The solid lines behind the genetic variants indicate the recombination rates in cM per Mb using HapMap controls. 13A. Association of variants in CLEC16A. 13B. Association of variants in C11orf30/LRR32. 13C. Association of variants in LPP. 13D. Association of variants in IL33.

DETAILED DESCRIPTION OF THE INVENTION

Figure 1A:
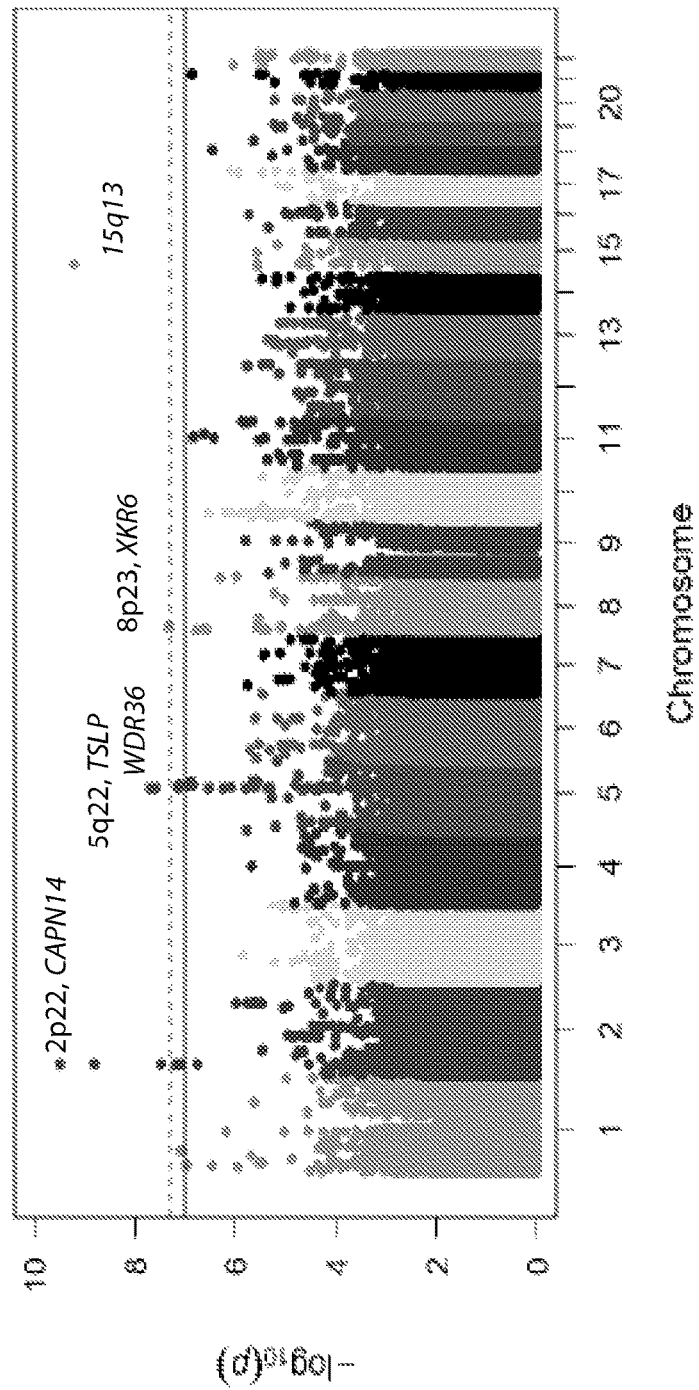
FIG. 1A. Data are from 736 subjects with eosinophilic esophagitis (EoE) and 9,246 controls having 1,468,075 genetic variants, with minor allele frequencies greater than 1% in the subjects with EoE. The −log of the probability is shown as a function of the genomic position of the autosomes. Genome-wide significance (dotted line, $p \leq 5 \times 10^{-8}$) and suggestive significance (solid line, $p \leq 10^{-7}$) are indicated.
Figure 1B:
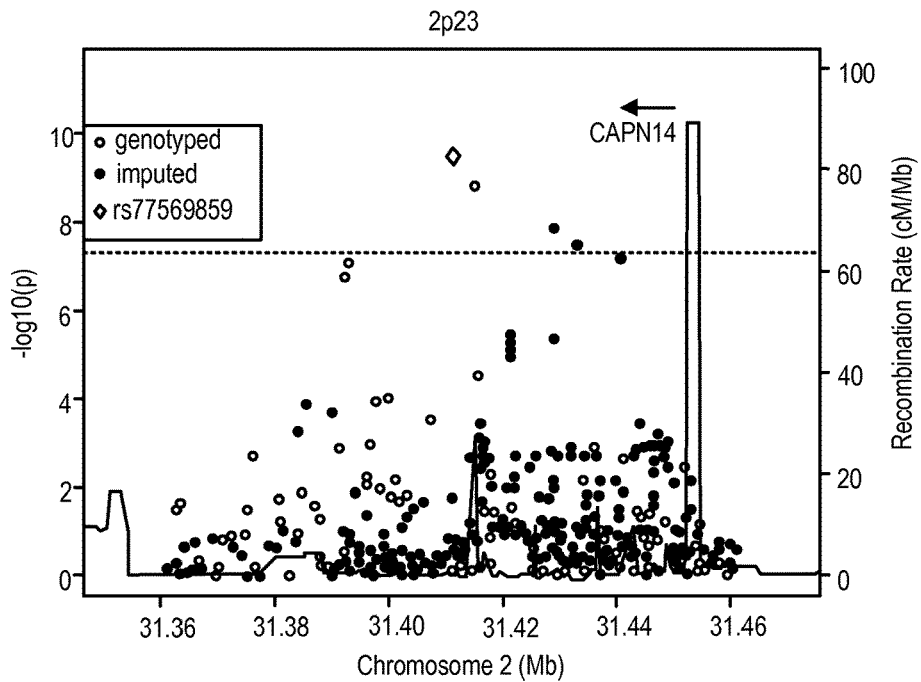
FIG. 1B. Genetic association of variants at the 2p23 locus with EoE risk.
Figure 1C:
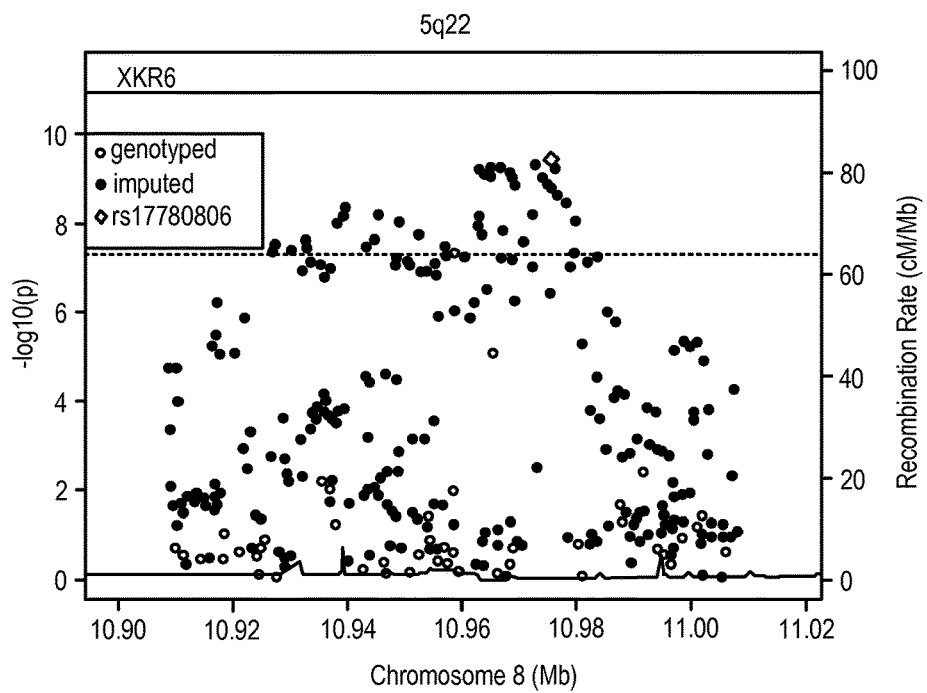
FIG. 1C. Genetic association of variants at the 5q22 locus with EoE risk.
Figure 1D:
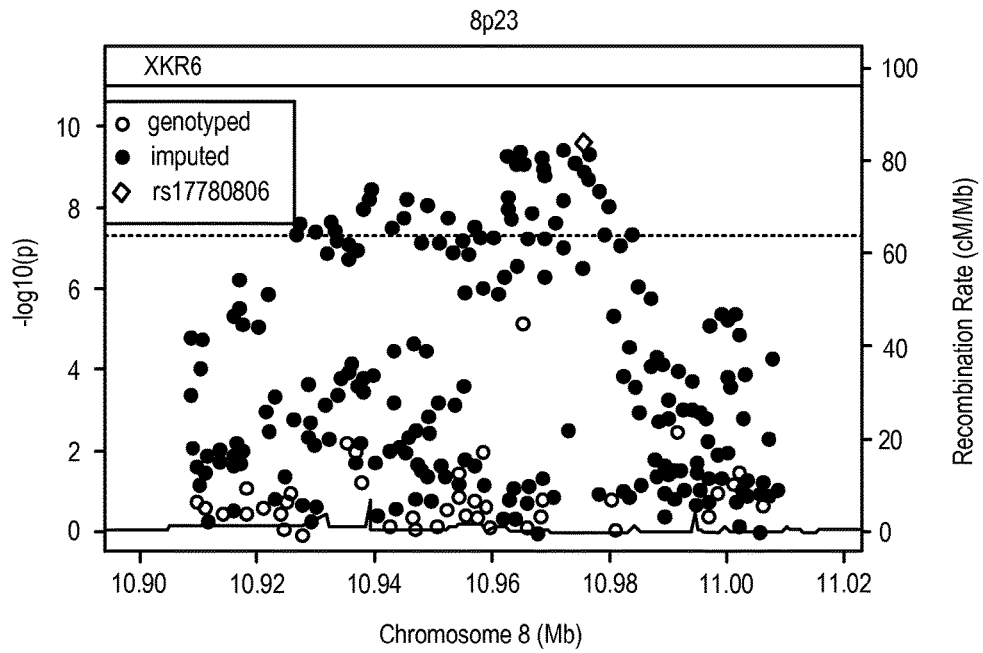
FIG. 1D. Genetic association of variants at the 8p23 locus with EoE risk.
Figure 1E:
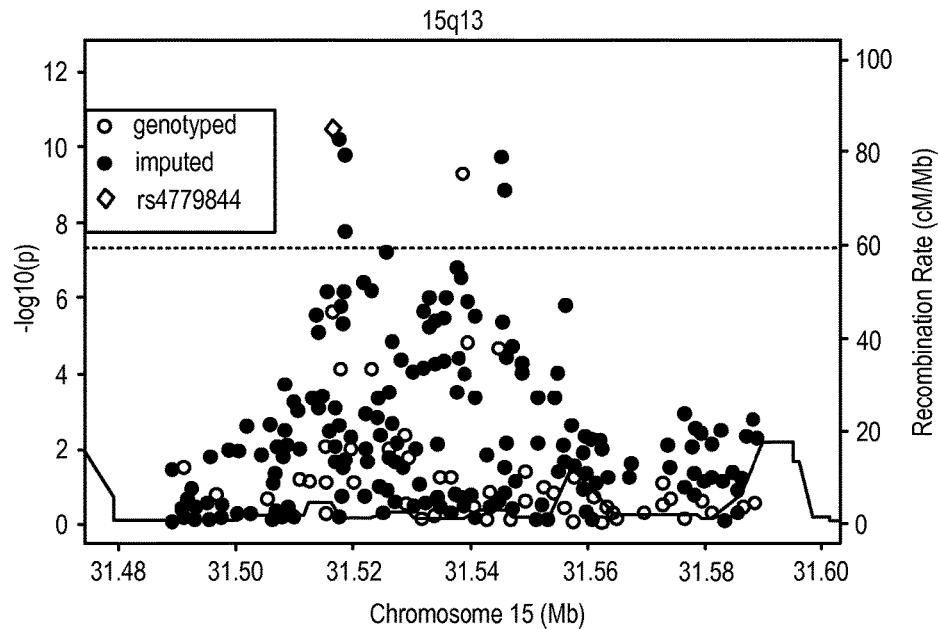
FIG. 1E. Genetic association of variants at the 15q13 locus with EoE risk. P-values ($-\log_{10}$) of the genetic association analysis of genotyped and imputed variants are plotted against the genomic positions of each genotyped and imputed SNPs on the x-axis on chromosomes 2, 5, 8, and 15. Genes in the region are shown above. The LD values ($r^2$) with the lead SNPs. The solid lines indicate the recombination rates in cM per Mb using subjects of European ancestry from the 1,000 genomes Project.

All references cited herein are incorporated by reference in their entirety. Also incorporated herein by reference in their entirety include: U.S. Patent Application No. 60/633,909, EOTAXIN-3 IN EOSINOPHILIC ESOPHAGITIS, filed on Dec. 27, 2004; U.S. Pat. No. 8,030,003, DIAGNOSIS OF EOSINOPHILIC ESOPHAGITIS BASED ON PRESENCE OF AN ELEVATED LEVEL OF EOTAXIN-3, issued Oct. 4, 2011 and filed as U.S. patent application Ser. No. 11/721,127 on Jun. 7, 2007; U.S. patent application Ser. No. 12/492,456, EVALUATION OF EOSINOPHILIC ESOPHAGITIS, filed on Jun. 26, 2009; U.S. patent application Ser. No. 12/628,992, IL-13 INDUCED GENE SIGNATURE FOR EOSINOPHILIC ESOPHAGITIS, filed on Dec. 1, 2009; U.S. Provisional Application No. 61/430,453, A STRIKING LOCAL ESOPHAGEAL CYTOKINE EXPRESSION PROFILE IN EOSINOPHILIC ESOPHAGITIS, filed on Jan. 6, 2011; U.S. patent application Ser. No. 13/051,873, METHODS AND COMPOSITIONS FOR MITIGATING EOSINOPHILIC ESOPHAGITIS BY MODULATING LEVELS AND ACTIVITY OF EOTAXIN-3, filed on Mar. 18, 2011; U.S. patent application Ser. No. 13/132,884, DETERMINATION OF EOSINOPHILIC ESOPHAGITIS, filed on Jun. 3, 2011; U.S. Provisional Application No. 61/497,796, NEGATIVE REGULATION OF EOSINOPHIL PRODUCTION BY TOLL-LIKE RECEPTORS, filed on Jun. 16, 2011; U.S. Patent Application No. 61/571,115, DIAGNOSTIC METHODS OF EOSINOPHILIC ESOPHAGITIS, filed on Jun. 21, 2011; U.S. Provisional Application No. 61/500,508, MOLECULAR DIAGNOSTIC PANEL OF EOSINOPHILIC GASTROINTESTINAL DISORDERS, filed on Jun. 23, 2011; U.S. patent application Ser. No. 13/132,295, METHODS OF DETERMINING EFFICACY OF GLUCOCORTICOID TREATMENT OF EOSINOPHILIC ESOPHAGITIS, filed on Aug. 22, 2011; PCT Patent Application No. US2012/020556, ESOPHAGEAL CYTOKINE EXPRESSION PROFILES IN EOSINOPHILIC ESOPHAGITIS, filed on Jan. 6, 2012; U.S. Provisional Application No. 61/602,897, ESOPHAGEAL MICRORNA EXPRESSION PROFILES IN EOSINOPHILIC ESOPHAGITIS, filed on Feb. 24, 2012; PCT Patent Application No. US2012/42985, BLOCKADE OF EOSINOPHIL PRODUCTION BY TOLL-LIKE RECEPTORS, filed on Jun. 18, 2012; PCT Patent Application No. US2012/043640, DIAGNOSTIC METHODS FOR EOSINOPHILIC ESOPHAGITIS, filed on Jun. 21, 2012; PCT Patent Application No. US2012/044061, MOLECULAR DIAGNOSTIC PANEL OF EOSINOPHILIC GASTROINTESTINAL DISORDERS, filed on Jun. 25, 2012; PCT Patent Application No. US2013/27503, ESOPHAGEAL MICRORNA EXPRESSION PROFILES IN EOSINOPHILIC ESOPHAGITIS, filed on Feb. 23, 2013; U.S. patent application Ser. No. 13/978,117, ESOPHAGEAL CYTOKINE EXPRESSION PROFILES IN EOSINOPHILIC ESOPHAGITIS, filed on Jul. 2, 2013; U.S. patent application No. TBD, BLOCKADE OF EOSINOPHIL PRODUCTION BY TOLL-LIKE RECEPTORS, filed on Dec. 13, 2013; U.S. patent application No. TBD, DIAGNOSTIC METHODS FOR EOSINOPHILIC ESOPHAGITIS, filed on Dec. 20, 2013; and U.S. patent application Ser. No. 14/128,887, MOLECULAR DIAGNOSTIC PANEL OF EOSINOPHILIC GASTROINTESTINAL DISORDERS, filed on Dec. 23, 2013.

Unless otherwise noted, terms are to be understood according to conventional usage by those of ordinary skill in the relevant art.

As used herein, the term "subject" refers to any member of the animal kingdom. In some embodiments, a subject is a human patient.

As used herein, the term "sample" encompasses a sample obtained from a subject or patient. The sample can be of any biological tissue or fluid. Such samples include, but are not limited to, sputum, saliva, buccal sample, esophageal swab, esophageal string test, throat swab, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a saliva spit, a buccal scrape, a buccal swab, a deep throat swab, exhaled breath condensate (EBC), and the like.

As used herein, "blood" can include, for example, plasma, serum, whole blood, blood lysates, and the like.

As used herein, the term "assessing" includes any form of measurement, and includes determining if an element is present or not. The terms "determining," "measuring,"

"evaluating," "assessing" and "assaying" can be used interchangeably and can include quantitative and/or qualitative determinations.

As used herein, the term "diagnosing or monitoring" with reference to a disease state or condition refers to a method or process of determining if a subject has or does not have a particular disease state or condition or determining the severity or degree of the particular disease state or condition.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present invention to mitigate a disease or a disorder in a host, preferably in a mammalian subject, more preferably in humans. Thus, the term "treatment" can include includes: preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted (see Webster's Ninth Collegiate Dictionary). Rather, as used herein, the term preventing refers to the ability of the skilled artisan to identify a population that is susceptible to disorders, such that administration of the compounds of the present invention can occur prior to onset of a disease. The term does not mean that the disease state must be completely avoided.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "expression levels" refers, for example, to a determined level of biomarker expression. The term "pattern of expression levels" refers to a determined level of biomarker expression compared either to a reference (e.g. a housekeeping gene or inversely regulated genes, or other reference biomarker) or to a computed average expression value (e.g. in DNA-chip analyses). A pattern is not limited to the comparison of two biomarkers but is more related to multiple comparisons of biomarkers to reference biomarkers or samples. A certain "pattern of expression levels" can also result and be determined by comparison and measurement of several biomarkers as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

A "single nucleotide polymorphism," or "SNP," is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI) or identifies the residue change associated with the identified polymorphism. SNP genotyping arrays have become an important tool for cohort identification and stratification, phenotype-genotype association studies, discovery of disease markers, prediction of molecular phenotypes, and clinical decision support.

As used herein, the term "variant" refers to a segment of DNA that differs from the reference DNA.

As used herein, the term "haplotype" refers to a segment of genomic DNA that is characterized by a specific combination of a series of polymorphic markers arranged along the segment. For diploid organisms such as humans, a haplotype comprises one member of the pair of alleles for each polymorphic marker or locus along the segment. In some embodiments, the haplotype can comprise an allele for each of two or more markers, three or more markers, four or more markers, or five or more markers.

As used herein, the terms "susceptibility" and "risk" refer to the proneness of an individual towards the development of a certain state (e.g. a certain trait, phenotype, or disease), or towards being less able to resist a particular state than the average individual. The term encompasses both increased susceptibility and decreased susceptibility. Thus, particular alleles at polymorphic markers and/or haplotypes of the invention as described herein can be characteristic of increased susceptibility (i.e. increased risk) of developing EoE, as characterized by a relative risk (RR) or odds ratio (OR) of greater than one for the particular allele or haplotype. Alternatively, some markers and/or haplotypes of the invention can be characteristic of decreased susceptibility (i.e. decreased risk) of developing EoE, as characterized by a relative risk of less than one.

A "nucleic acid sample" as described herein, refers to a sample obtained from an individual that contains nucleic acid (DNA or RNA). In certain embodiments, such as, for example, the detection of specific polymorphic markers and/or haplotypes, the nucleic acid sample comprises genomic DNA. Such a nucleic acid sample can be obtained from any source that contains genomic DNA, including a blood sample, sample of amniotic fluid, sample of cerebrospinal fluid, or tissue sample from skin, muscle, buccal or conjunctival mucosa, placenta, gastrointestinal tract, or other organs.

"Therapeutic" and "therapeutics" as used herein refers primarily to one or more anesthetic, analgesic, and/or opioid compositions having an actual or potential beneficial effect for a patient. In some embodiments, the term can also include accompanying modes of treatment and/or administration and/or co-administration with other compositions and/or treatments, as recognized by those of skill in the art of anesthesia and analgesia.

Eosinophilic esophagitis (EoE) is an emerging chronic inflammatory disorder associated with allergic hypersensitivity to food. Consistent with an allergic etiology, EoE frequently co-occurs with allergic diseases, including asthma, eczema, allergic rhinitis and food anaphylaxis (Rothenberg, M. E. *Gastroenterology* 137:1238-49 (2009); Collins, M. H. et al. *Clin Gastroenterol Hepatol* 6:621-9 (2008); Putnam, P. E. and Rothenberg, M. E. *Curr Gastroenterol Rep* 11:220-5 (2009)). The reason EoE patients develop a tissue-specific allergic response remains unclear, as the currently identified inflammatory pathways and genes in EoE and other allergic diseases overlap.

The only EoE genome-wide association study (GWAS) reported to identified a single significant susceptibility locus at 5q22, which harbors the gene for thymic stromal lymphopoietin, TSLP (Rothenberg, M. E. et al. *Nat Genet* 42:289-91 (2010)). A candidate gene analysis confirmed the association of EoE with TSLP as well as its receptor CRLF2 (cytokine receptor-like factor 2) (Sherrill, J. D. et al. *J Allergy Clin Immunol* 126:160-5 e3 (2010); Zuo, L. et al. *J Immunol* 185:660-9 (2010)). Candidate gene studies have shown that CCL26 (eotaxin-3) and FLG (filaggrin) (Blanchard, C. et al. *J Immunol* 184:4033-41 (2010); Blanchard, C. et al. *J Clin Invest* 116:536-47 (2006)) are associated with EoE susceptibility. However, genetic variations in these genes and 5q22 have also been linked with other atopic disorders (McAleer, M. A. and Irvine, A. D. *J Allergy Clin Immunol* 131:280-91 (2013); Fallon, P. G. et al. *Nat Genet* 41:602-8 (2009); Shin, H. D. et al. *Hum Mol Genet* 12:1279-85 (2003)), further indicating that genetics can contribute to the tissue specificity of this allergic disorder.

As described herein, a GWAS of single-nucleotide polymorphisms (SNPs) from >2.5 million genetic markers was performed on European ancestry EoE cases followed by a multi-site replication cohort (NIH Consortium of Food Allergy Research (CoFAR)) with local and out-of-study control subjects. This GWAS greatly expanded the number of EoE cases (from 351 to 736) and controls (from 3105 to 9246) of the previous study. Additional susceptibility loci for EoE were identified that underscore the interconnection with atopic sensitization; an EoE-specific linkage was identified that mechanistically connects Th2 immunity with an esophageal-specific pathway involving calpain 14 (CAPN14) in disease pathoetiology.

In addition to replication of the 5q22 locus (meta-analysis $p=1.9\times10^{-16}$), strong associations of multiple variants were identified, including 2p23 (encoding CAPN14, $p=2.5\times10^{-10}$), 8p23 (encoding XKR6, $p=4.8\times10^{-8}$), and 15q13 (in a gene desert, $p=6.3\times10^{-10}$). CAPN14 was specifically expressed in the esophagus, dynamically upregulated as a function of disease activity and genetic haplotype and after exposure of epithelial cells to IL-13, and located in an epigenetic hotspot modified by IL-13. Additional candidate loci 1p13, 5q23, 10p12, 11q13, 11q14, and 21q22 ($p<5\times10^{-7}$) were also identified. There was enriched esophageal expression ($p<10^{-4}$) of the genes neighboring the top 208 sequence variants associated with disease susceptibility ($p<10^{-4}$). Nine of 22 recently identified allergic sensitization loci were associated with EoE susceptibility ($4.8\times10^{-2}<p<5.1\times10^{-11}$). Taken together, this study has identified four novel susceptibility loci for EoE, the strongest association being with CAPN14. The interplay of allergic sensitization can therefore be linked with an EoE-specific IL-13-inducible esophageal response involving CAPN14.

A GWAS was performed on SNPs from >2.5 million genetic markers, allowing for the identification of additional susceptibility loci for EoE that underscore the interconnection with atopic sensitization and identify an EoE-specific linkage that mechanistically connects Th2 immunity with an esophageal specific pathway involving CAPN14 in disease pathoetiology. Markers in 2p23, 5q22, 8p23, and 15q13 reached genome-wide significance ($p<5\times10-8$). The variants most highly associated with increased risk of EoE were found at 2p23 spanning the CAPN14 gene (best SNP-rs77569859, $p=3.30\times10-10$ OR=1.98). This region was imputed to a composite reference panel from 1000 genomes in order to identify the commonly-occurring variants (MAF>1%) on the risk haplotype that could be driving the genetic association; this study found that no haplotype of continuous SNPs or haplotype constructed using the most associated variants in the region was more highly associated with EoE risk than rs77569859 alone (best haplotype p-value=$3.5\times10-8$, OR=1.6). Variants at the other two loci reaching genome-wide significance were located at the XKR6 gene (8p23) and in a gene desert (15q13). Very little is known about the XK, Kell blood group complex subunit-related family, member 6 (XKR6); however, public expression databases report expression in the immune compartment. These four genome-wide susceptibility loci remained associated with EoE, and the effect size was not significantly influenced after correcting for atopy.

Using an independently ascertained cohort that did not overlap with the first EoE GWAS, there was strong replication of disease linkage with 5q22 (rs6594499, Fishers combined p-value=$1.9\times10-16$). After imputing the region to account for all common genetic variation (MAF>1%), the most significant association with the development of EoE was found to be downstream of TSLP and WDR36 at rs1438672, with 12 variants having a P<0.01 after adjusting for the most significant variant. In contrast to the EoE susceptibility locus which spanned the TSLP and WDR36 genes, 5q22 variants associated with allergic sensitization, atopic dermatitis, and allergic rhinitis have all been shown to be upstream of the TSLP gene and the reported association of this locus with asthma is more limited than the association seen in EoE, suggesting that different genetic etiologies are driving the associations at this locus.

Variants at 1p13, 5q23, 10p12, 11q13, 11q14, and 21q22 demonstrated suggestive genetic association with EoE risk ($p<10-7$). After establishing statistical associations between genetic variants at these loci with EoE risk, fine mapping studies were performed starting with genotype imputation of common variants (MAF>0.01) that were not captured in the combined GWAS dataset. The 11q13 association was identified in asthma, atopic dermatitis, inflammatory bowel disease, allergic rhinitis, and sensitization to grass. The EoE-associated variants at 11q13 are between C11orf30 and LRRC32. LRRC32 (the leucine-rich repeat containing 32 gene, also known as GARP) has a role in latent TGF-β surface expression, and LRRC32 mRNA is highly expressed in activated FOXP3+ regulatory T cells. It is notable that TGF-β and FOXP3+T regulatory cells have been implicated in EoE.

Figure 12A:
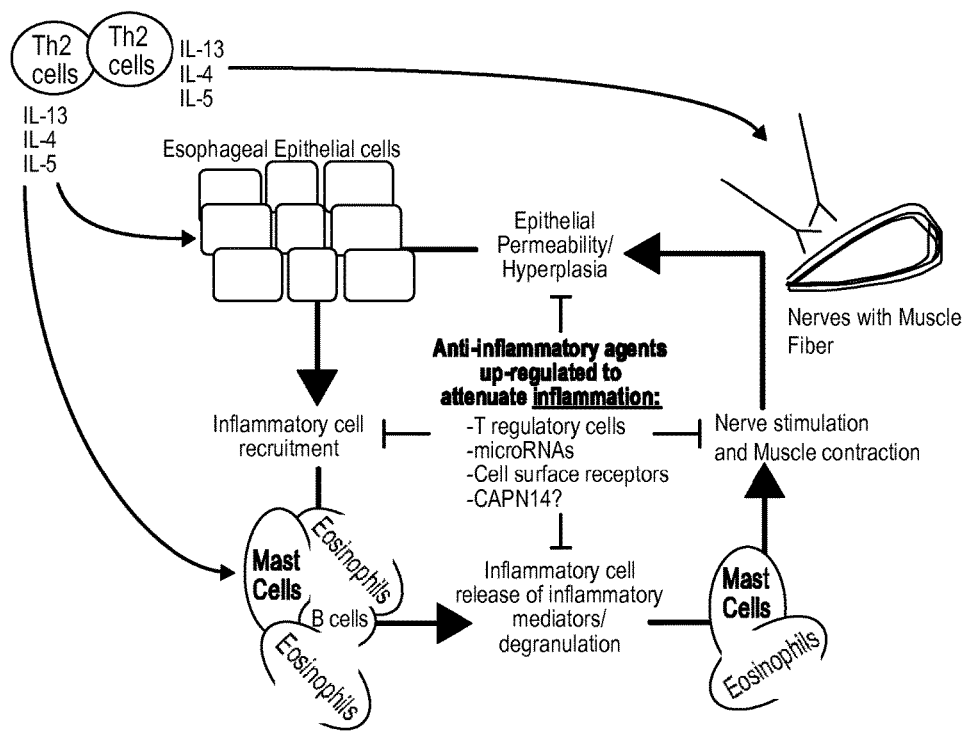
FIG. 12A. A model in which CAPN14 is induced along with other anti-inflammatory agents such as microRNAs, cell surface receptors, and T regulatory cells; Together, the data presented in the preceding figures are consistent with this model.
Figure 12B:
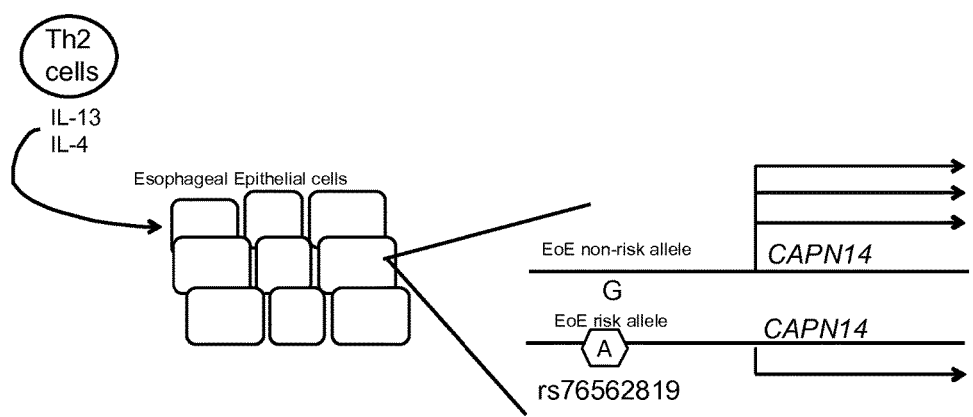
FIG. 12B. When exposed to IL-13 and IL-4, chromosomes in epithelial cells with the CAPN14 EoE risk allele are unable to induce CAPN14 expression to the extent of chromosomes with the nonrisk allele. A model is proposed in which the allelic change in CAPN14 expression dysregulates a critical negative feedback loop in the esophagus, resulting in increased risk of pathology and EoE.
Figure 14:
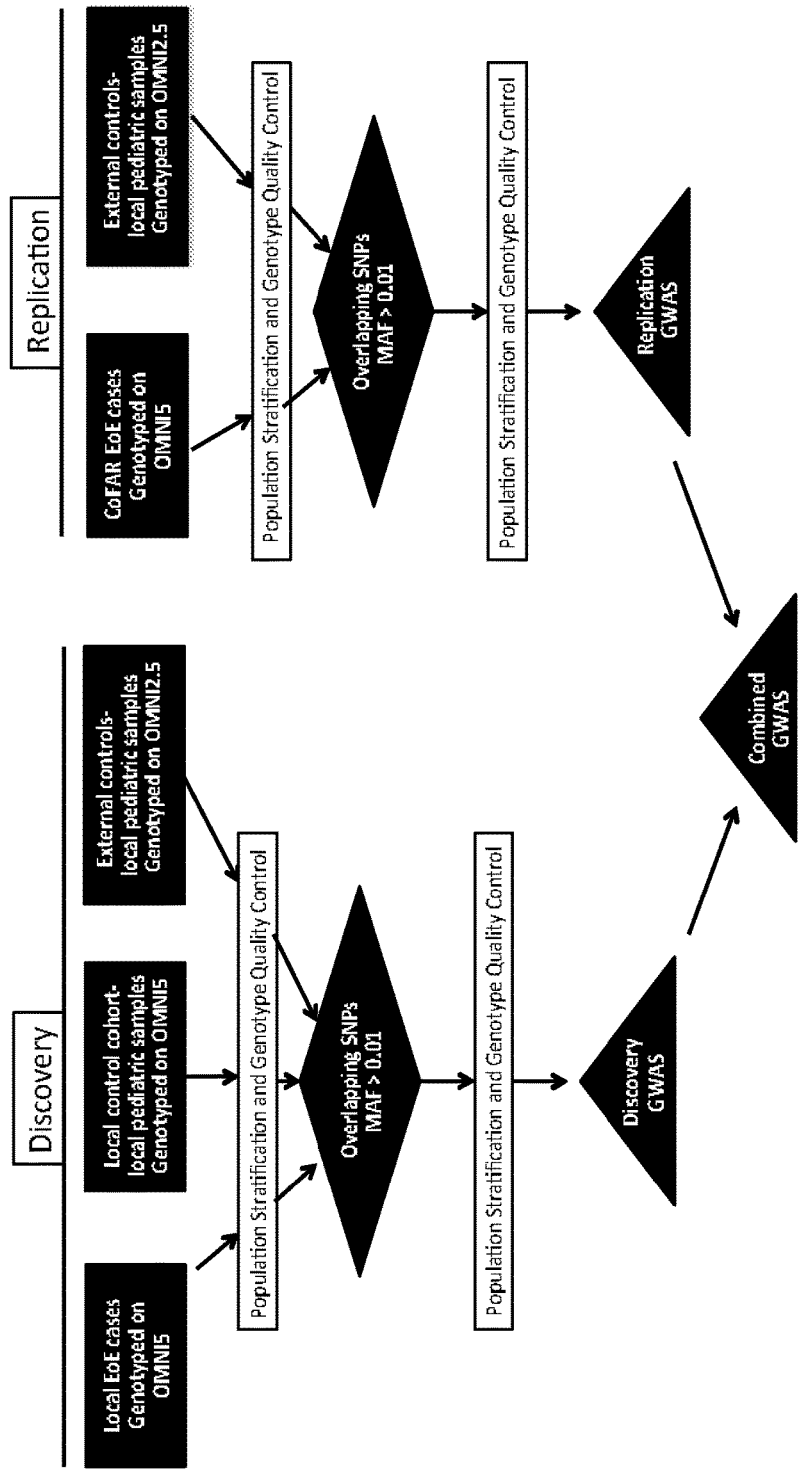
FIG. 14. Flow chart of the EoE GWAS analytical pipeline. External controls from University of Michigan (acquired through dbGAP) were randomly assigned to Discovery and Replication cohorts. CoFAR: NIH Consortium of Food Allergy Research (CoFAR); EoE: eosinophilic esophagitis; GWAS: genome-wide association study; MAF: minor allele frequency; SNP: single nucleotide polymorphism.

In addition, the current study identified statistically significant association of genetics variants known to be associated with allergic sensitization with the development of EoE. Of the 22 known atopy loci, 9 were found to also be associated with EoE (Table 10), underscoring the key role of atopy in EoE, and 8 of these SNPs were associated with comparable disease risk effects. The atopic sensitization loci with the greatest association with EoE were at CLEC16A, LRRC32, LPP (C-type lectin domain family 16, member A, Leucine rich repeat containing 32, LIM domain containing preferred translocation partner in lipoma), and TSLP/WDR36 (FIGS. 1 and 12). Of the ten replicated loci that linked with EoE in this study, only two overlapped with the 22 allergic sensitization loci, highlighting that non-atopy related processes can be operational.

In conclusion, as described herein, four established susceptibility loci for EoE have been determined, with compelling evidence for six other loci. Importantly, these data substantiate a mechanism to explain the tissue-specific manifestations of this prototypic allergic disease. In particular, evidence is provided for the interaction of shared genetic and molecular pathways between general atopy risk factors (e.g. TSLP/WDR36, LRR32, IL-33, LPP) and EoE disease-specific elements, most notably genetic risk factors present at 2q23 where CAPN14 is located. This also allows for the measurement of CAPN14 expression to be used in EoE diagnostic and monitoring tests.

As disclosed herein, particular marker alleles or haplotypes, and markers in linkage disequilibrium therewith, can be associated with EoE. In some embodiments, the marker allele or haplotype is one that confers a significant risk or susceptibility to developing EoE. In some embodiments, one or more marker alleles are selected from those listed in any of Tables 2-5 and 7-10. In some embodiments, one or more marker alleles are selected from those located at 2q23 CAPN14, 5q22 TSLP, 8p23 XKR6, and/or 15q13. In some embodiments, one or more marker alleles are selected from those located at 1p13, 5q23, 10p12, 11q13, 11q14, and/or 21q22. In some embodiments, one or more marker alleles are selected from the CAPN14 gene. In some embodiments, the one or more marker alleles selected from the CAPN14 gene can be selected from rs77569859, rs10192210, rs76562819, and rs75960361. In some embodiments, one or more marker alleles are selected from TSLP rs3806933, TSLP rs6594499, XKR6 rs2898261, SLC25A24 rs2000260, rs8041227 located between LOC283710 and KLF13, and rs1438672 located between TSLP and WDR36. In some embodiments, one or more marker alleles are associated with atopy. In some embodiments, one or more marker associated with atopy is selected from Table 10.

Embodiments of the invention encompass methods of determining a risk or a susceptibility to developing EoE in a subject, the method including: obtaining a nucleic acid sample from a subject; analyzing the sample for presence or absence of at least one allele of at least one polymorphism associated with EoE, wherein the presence of the at least one allele of at least one polymorphism associated with EoE indicates that the subject has an elevated risk for suffering from EoE. In some embodiments, a subject who is determined to have an elevated risk for suffering from EoE is subsequently evaluated in order to provide a diagnosis of EoE. In some embodiments, a subject diagnosed with EoE is treated for EoE. In some embodiments, providing a diagnosis of EoE involves measuring CAPN14 expression.

Embodiments of the invention also encompass methods of treating EoE in a subject, the method including: obtaining a nucleic acid sample from a subject; analyzing the sample for presence or absence of at least one allele of at least one polymorphism associated with EoE, wherein the presence of the at least one allele of at least one polymorphism associated with EoE indicates that the subject has an elevated risk for suffering from EoE; evaluating a subject who is determined to have an elevated risk for suffering from EoE in order to provide a diagnosis of EoE; and treating a subject who is diagnosed with EoE for EoE.

Accordingly, the methods and materials of the invention are expressly contemplated to be used both alone and in combination with other tests and indicia, whether quantitative or qualitative in nature.

In some embodiments of the methods, the at least one polymorphism associated with EoE can occur at, for example, the following variants: 5q22, encoding TSLP; 2q23, encoding CAPN14, 8p23, encoding XKR6; and 15q13. In some embodiments of the methods, the at least one polymorphism associated with EoE can occur at, for example, the following variants: 1p13, 5q23, 10p12, 11q13, 11q14, and 21q22. In some embodiments of the methods, the at least one polymorphism associated with EoE is selected from those listed in any of Tables 2-5 and 7-10. In some embodiments, the at least one polymorphism associated with EoE is selected from those located at 2q23 CAPN14, 5q22 TSLP, 8p23 XKR6, and/or 15q13. In some embodiments, the at least one polymorphism associated with EoE is selected from those located at 1p13, 5q23, 10p12, 11q13, 11q14, and/or 21q22. In some embodiments, the at least one polymorphism associated with EoE is selected from the CAPN14 gene. In some embodiments, the at least one polymorphism associated with EoE selected from the CAPN14 gene can be selected from rs77569859, rs10192210, rs76562819, and rs75960361. In some embodiments, the at least one polymorphism associated with EoE is selected from TSLP rs3806933, TSLP rs6594499, XKR6 rs2898261, SLC25A24 rs2000260, rs8041227 located between LOC283710 and KLF13, and rs1438672 located between TSLP and WDR36.

In some embodiments, the sample can be analyzed for presence or absence of at least two polymorphisms associated with EoE. In some embodiments, the sample can be analyzed for presence or absence of at least three polymorphisms associated with EoE. In some embodiments, the sample can be analyzed for presence or absence of at least four polymorphisms associated with EoE. In some embodiments, the sample can be analyzed for presence or absence of five or more polymorphisms associated with EoE.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called SNPs.

Reference can be made to different alleles at a polymorphic site without choosing a reference allele. Alternatively, a reference sequence can be referred to for a particular polymorphic site. The reference allele can be referred to as the "wild-type" allele, and it usually is chosen as either the first sequenced allele or as the allele from a "non-affected" individual (e.g. an individual that does not display a trait or disease phenotype).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e. a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. Haplotypes can comprise a combination of various polymorphic markers, e.g. SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g. Chen, X. et al., *Genome Res.* 9(5): 492-98 (1999); Kutyavin et al., *Nucleic Acid Res.* 34:e128 (2006)), utilizing PCR, LCR, Nested PCR, and other techniques for nucleic acid amplification, and direct sequencing. Specific commercial methodologies available for SNP genotyping include, but are not limited to, TaqMan genotyping assays and SNPlex platforms (Applied Biosystems), gel electrophoresis (Applied Biosystems), mass spectrometry (e.g. MassARRAY system from Sequenom), minisequencing methods, real-time PCR, Bio-Plex system (BioRad), CEQ and SNPstream systems (Beckman), array hybridization technology (e.g. Affymetrix GeneChip; Perlegen), BeadArray Technologies (e.g. Illumina GoldenGate and Infinium assays), array tag technology (e.g. Parallele), and endonuclease-based fluorescence hybridization technology (Invader; Third Wave). Thus, by use of these or other methods available to the person skilled in the art, one or more alleles at polymorphic markers, including microsatellites, SNPs, or other types of polymorphic markers, can be identified.

Linkage Disequilibrium

Linkage disequilibrium (LD) refers to a non-random assortment of two genetic elements. For example, if a particular genetic element (e.g. an allele of a polymorphic marker, or a haplotype) occurs in a population at a frequency of 0.50 (50%), and another element occurs at a frequency of 0.50 (50%), then the predicted occurrence of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g. allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g. human populations, individuals will typically have two alleles or allelic combinations for each genetic element (e.g. a marker, haplotype, or gene).

Many different measures have been proposed for assessing the strength of linkage disequilibrium (reviewed in Devlin, B. & Risch, N., *Genomics* 29:311-22 (1995)). Most capture the strength of association between pairs of bi-allelic sites. Two important pairwise measures of LD are $r^2$ (sometimes denoted $\Delta^2$) and $|D'|$ (Lewontin, R., *Genetics* 49:49-67 (1964); Hill, W. G. & Robertson, *A. Theor. Appl. Genet.* 22:226-231 (1968)). Both measures range from 0 (no disequilibrium) to 1 ("complete" disequilibrium), but their interpretation is slightly different. $|D'|$ is defined in such a way that it is equal to 1 if just two or three of the possible haplotypes are present, and it is <1 if all four possible haplotypes are present. Therefore, a value of $|D'|$ that is <1 indicates that historical recombination can have occurred between two sites (recurrent mutation can also cause $|D'|$ to be <1, but for SNPs, this is typically regarded as being less likely than recombination). The measure $r^2$ represents the statistical correlation between two sites and takes the value of 1 if only two haplotypes are present.

The $r^2$ measure is a relevant measure for association mapping because there is a simple inverse relationship between $r^2$ and the sample size sufficient to detect association between susceptibility loci and SNPs. These measures are defined for pairs of sites, but, for some applications, a determination of how strong LD is across an entire region that contains many polymorphic sites can be desirable (e.g. testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be sufficient under a particular population model to generate the LD that is seen in the data. This type of method can also provide a statistically rigorous approach to the problem of determining whether LD data provide evidence for the presence of recombination hotspots. For the methods described herein, a significant $r^2$ value can be at least 0.1, such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In some embodiments, the significant $r^2$ value can be at least 0.2. Alternatively, linkage disequilibrium as described herein refers to linkage disequilibrium characterized by |D'| values of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or |D'| ($r^2$ up to 1.0 and |D'| up to 1.0). In some embodiments, linkage disequilibrium is defined in terms of values for both the $r^2$ and |D'| measures. In some embodiments, a significant linkage disequilibrium is defined as $r^2>0.1$ and |D'|>0.8. In some embodiments, a significant linkage disequilibrium is defined as $r^2>0.2$ and |D'|>0.9. Other combinations and permutations of values of $r^2$ and |D'| for determining linkage disequilibrium are also contemplated, and are also within the scope of embodiments of the invention. Linkage disequilibrium can be determined in a single human population, as defined herein, or it can be determined in a collection of samples comprising individuals from more than one human population. In some embodiments, LD is determined in a sample from one or more of the HapMap populations (Caucasian, African, Japanese, Chinese) (as defined at http <colon slash slash> www <dot> hapmap <dot> org).

If all polymorphisms in the genome were independent at the population level (i.e. no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms can give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, et al., *Proc Natl Acad Sci USA* 99:2228-2233 (2002); Reich, et al., *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, et al., *Nature Genet.* 29:229-232 (2001); Gabriel, et al., *Science* 296:2225-2229 (2002); Patil, et al., *Science* 294: 1719-1723 (2001); Dawson, et al., *Nature* 418:544-548 (2002); Phillips, et al., *Nature Genet.* 33:382-387 (2003)).

There are two main methods for defining these haplotype blocks: blocks can be defined as regions of DNA that have limited haplotype diversity (see, e.g., Daly, et al., *Nature Genet.* 29:229-232 (2001); Patil, et al., *Science* 294:1719-1723 (2001); Dawson, et al., *Nature* 418:544-548 (2002); Zhang, et al., *Proc. Natl. Acad. Sci. USA* 99:7335-7339 (2002)), or as regions between transition zones having extensive historical recombination, identified using linkage disequilibrium (see, e.g., Gabriel, et al., *Science* 296:2225-2229 (2002); Phillips, et al., *Nature Genet.* 33:382-387 (2003); Wang, et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, et al., *Science* 310:321-32324 (2005); Myers, et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and a set of "tagging" SNPs or markers (the smallest set of SNPs or markers sufficient to distinguish among the haplotypes) can then be identified. These tagging SNPs or markers can then be used in assessment of samples from groups of individuals, in order to identify association between the phenotype and haplotype. If desired, neighboring haplotype blocks can be assessed concurrently, as there can also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait and as such are useful for use in the methods and kits of the present invention. One or more causative (functional) variants or mutations can reside within the region found to be associating to the disease or trait. The functional variant can be another SNP, a tandem repeat polymorphism (such as a minisatellite or a microsatellite), a transposable element, or a copy number variation, such as an inversion, deletion, or insertion. Such variants in LD with the variants described herein can confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in some embodiments of the invention, markers that are in LD with the markers and/or haplotypes of the invention, as described herein, can be used as surrogate markers. The surrogate markers have in some embodiments relative risk (RR) and/or odds ratio (OR) values smaller than for the markers or haplotypes initially found to be associating with the disease, as described herein. In some embodiments, the surrogate markers have RR or OR values greater than those initially determined for the markers initially found to be associating with the disease, as described herein. An example of such an embodiment would be a rare or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well-known to the person skilled in the art and are therefore within the scope of the present invention.

Relationship Between Risk and Disease

As disclosed herein, an individual who is at an increased susceptibility (i.e. increased risk) for a disease or trait is an individual in whom at least one specific allele at one or more polymorphic marker or haplotype conferring increased susceptibility (increased risk) for the disease or trait is identified (i.e. at-risk marker alleles or haplotypes). The at-risk marker or haplotype is one that confers an increased risk (increased susceptibility) of the disease. In some embodiments, significance associated with a marker or haplotype is measured by a relative risk (RR). In some embodiments, significance associated with a marker or haplotype is measured by an odds ratio (OR). In a further embodiment, the significance is measured by a percentage. In some embodiments, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In some embodiments, a risk (relative risk and/or odds ratio) of at least 1.2 is significant. In some embodiments, a risk of at least 1.3 is significant. In some embodiments, a risk of at least 1.4 is significant. In some embodiments, a relative risk of at least 1.5 is significant. In some embodiments, a significant increase in risk is at least 1.7 is significant. However, other cutoffs are also contemplated, e.g. at least 1.15, 1.25, 1.35, and so on, and such cutoffs are also within scope of the present invention. In some embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In some embodiments, a significant increase in risk is at least 20%. In some embodiments, a significant increase in risk is at least 30%, at least 40%, at least 50%, at least 60%, at least 70%, at least 80%, at least 90%, and at least 100%. Other cutoffs or ranges as deemed suitable by the person skilled in the art to characterize the invention are however also contemplated, and those are also within scope of the present invention. In some embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype as described herein is one where at least one allele of at least one marker or haplotype is more frequently present in an individual at risk for the disease (or trait) (affected), or diagnosed with the disease, compared to the frequency of its presence in a comparison group (control), such that the presence of the marker or haplotype is indicative of susceptibility to the disease. In some embodiments, the control group can be a population sample, i.e. a random sample from the general population. In some embodiments, the control group is represented by a group of individuals who are disease-free. In some embodiments, such disease-free controls can be characterized by the absence of one or more specific disease-associated symptoms. Alternatively, the disease-free controls are those that have not been diagnosed with the disease. In some embodiments, the disease-free control group is characterized by the absence of one or more disease-specific risk factors. In some embodiments, such risk factors include at least one environmental risk factor. Representative environmental factors are natural products, minerals, or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In some embodiments, the risk factors comprise at least one additional genetic risk factor.

An example of a simple test for correlation would be a Fisher-exact test on a two by two table. Given a cohort of chromosomes, the two by two table is constructed out of the number of chromosomes that include both of the markers or haplotypes, one of the markers or haplotypes but not the other, and neither of the markers or haplotypes. Other statistical tests of association known to the skilled person are also contemplated and are also within scope of the invention.

In some embodiments of the invention, an individual who is at a decreased susceptibility (i.e. at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In some embodiments, the protective marker or haplotype is one that confers a significant decreased risk (or susceptibility) of the disease or trait.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

Determination of Risk

The creation of a model to calculate the overall genetic risk involves two steps: i) conversion of odds-ratios for a single genetic variant into relative risk, and ii) combination of risk from multiple variants in different genetic loci into a single relative risk value.

Most gene discovery studies for complex diseases or traits that have been published to date in authoritative journals have employed a case-control design due to their retrospective setup. These studies sample and genotype a selected set of cases (people who have the specified disease condition) and control individuals. The interest is in genetic variants (alleles) whose frequency in cases and controls differ significantly.

The results are typically reported in odds ratios, which describe the ratio between the fraction (probability) with the risk variant (carriers) versus the non-risk variant (non-carriers) in the groups of affected versus the controls, i.e. expressed in terms of probabilities conditional on the affection status:

$$OR = (Pr(c|A)/Pr(nc|A))/(Pr(c|C)/Pr(nc|C))$$

In some embodiments, the absolute risk for the disease or trait is what is determined, i.e. the fraction of those individuals carrying the risk variant who get the disease or, in other words, the probability of getting the disease. This number cannot be directly measured in case-control studies, in part because the ratio of cases versus controls is typically not the same as that in the general population. However, under certain assumptions, the risk can be calculated from the odds ratio value.

When genotypes of many SNP variants are used to estimate the risk for an individual, unless otherwise stated, a multiplicative model for risk can be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A) \text{ and } Pr(g1,g2)=Pr(g1)Pr(g2)$$

In embodiments where markers are closely spaced on the genome, i.e. are in linkage disequilibrium such that the concurrence of two or more risk alleles is correlated, a haplotype modeling where the odds-ratios are defined for all allele combinations of the correlated SNPs can be employed.

As an example, consider an individual who has the following genotypes at four markers associated with risk of type-2 diabetes along with the risk relative to the population at each marker:

Chromo 3 PPARG CC Calculated risk: RR(CC)=1.03
Chromo 6 CDKAL1 GG Calculated risk: RR(GG)=1.30
Chromo 9 CDKN2A AG Calculated risk: RR(AG)=0.88
Chromo 11 TCF7L2 TT Calculated risk: RR(TT)=1.54

Combined, the overall risk relative to the population for this individual is: $1.03\times1.30\times0.88\times1.54=1.81$.

Determination of Susceptibility to EoE

As disclosed herein, certain polymorphic markers and haplotypes comprising such markers are found to be useful for risk assessment of susceptibility to EoE. Risk assessment can involve the use of the markers for determining a susceptibility to EoE. Particular alleles of polymorphic markers (e.g. SNPs) are found more frequently in individuals with particular susceptibility to such diseases. Therefore, these marker alleles have predictive value for determining whether these individuals will suffer from EoE. Tagging markers in linkage disequilibrium with at-risk variants (or protective variants) as disclosed herein can be used as surrogates for these markers (and/or haplotypes). Such surrogate markers can be located within a particular haplotype block or LD block. Such surrogate markers can also sometimes be located outside the physical boundaries of such a haplotype block or LD block, either in close vicinity of the LD block/haplotype block or possibly also located in a more distant genomic location.

For the SNP markers described herein, the opposite allele to the allele found to be in excess in patients (at-risk allele) is found in decreased frequency in situations where EoE is observed. These markers and haplotypes in LD are thus protective for EoE, i.e. they confer a decreased risk or susceptibility of individuals carrying these markers and/or haplotypes developing EoE.

In some embodiments, variants as disclosed herein, including certain haplotypes, can comprise a combination of various genetic markers, e.g. SNPs and microsatellites. Detecting haplotypes can be accomplished by methods known in the art and/or described herein for detecting sequences at polymorphic sites. Furthermore, correlation between certain haplotypes or sets of markers and disease phenotypes can be verified using standard techniques. A representative example of a simple test for correlation would be a Fisher-exact test on a two by two table.

In some embodiments, a marker allele or haplotype found to be associated with EoE is one in which the marker allele or haplotype is more frequently present in an individual at risk for suffering from EoE (affected), compared to the frequency of its presence in a healthy individual (control), or in a randomly selected individual from the population, wherein the presence of the marker allele or haplotype is indicative of a susceptibility to suffering from EoE. In some embodiments, at-risk markers in linkage disequilibrium with one or more markers shown herein to be associated with suffering from EoE (e.g. marker alleles as listed in any of Tables 2-5 and 7-10) are tagging markers that are more frequently present in an individual at risk for suffering from EoE (affected), compared to the frequency of their presence in a healthy individual (control) or in a randomly selected individual from the population, wherein the presence of the tagging markers is indicative of increased susceptibility to suffering such effects. In some embodiments, at-risk marker alleles (i.e. conferring increased susceptibility) in linkage disequilibrium with one or more markers found to be associated with EoE are markers comprising one or more allele that is more frequently present in an individual at risk for suffering such effects, compared to the frequency of their presence in a healthy individual (control), wherein the presence of the markers is indicative of increased susceptibility to suffering from EoE.

In embodiments of the invention, the methods comprise obtaining a sample containing genomic DNA from an individual for analysis. The sample can be, for example, a buccal swab, a saliva sample, a blood sample, or other suitable samples containing genomic DNA, as disclosed herein, and the like. The genomic DNA can be analyzed using any common technique available to the skilled person, such as, for example, high-throughput or low density array technologies, and the like. Results from such genotyping can subsequently be analyzed for the presence of certain variants known to be susceptibility variants for a particular condition, such as the genetic variants disclosed herein. Calculating risk conferred by a particular genotype for the individual can be based on comparing the genotype of the individual to previously determined risk (expressed as a relative risk (RR) or an odds ratio (OR), for example) for the genotype, for example for a heterozygous carrier of an at-risk variant for a particular condition or trait (such as for EoE). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. In some embodiments, using the population average can be more convenient, since it provides a measure which is easy to interpret for the user, i.e. a measure that gives the risk for the individual, based on his/her genotype, compared with the average in the population.

Overall risk for multiple risk variants can be performed using standard methodology. For example, assuming a multiplicative model, i.e. assuming that the risk of individual risk variants multiply to establish the overall effect, allows for a straightforward calculation of the overall risk for multiple markers.

The detection of the particular genetic marker alleles that make up particular haplotypes in the sample can be performed by a variety of methods as described herein and/or known in the art. For example, genetic markers can be detected at the nucleic acid level (e.g. by direct nucleotide sequencing or by other genotyping means known to the skilled in the art) or at the amino acid level if the genetic marker affects the coding sequence of a protein (e.g. by protein sequencing or by immunoassays using antibodies that recognize such a protein). The marker alleles or haplotypes disclosed herein correspond to fragments of genomic segments (e.g. genes) associated with development of EoE. Such fragments encompass the DNA sequence of the polymorphic marker or haplotype in question but can also include DNA segments in strong LD (linkage disequilibrium) with the marker or haplotype.

In embodiments of the invention, a test sample containing genomic DNA obtained from the subject is collected, and PCR is used to amplify a fragment comprising one or more markers or haplotypes of the present invention. Identification of a particular marker allele or haplotype can be accomplished using a variety of methods (e.g. sequence analysis, analysis by restriction digestion, specific hybridization, single-stranded conformation polymorphism assays (SSCP), electrophoretic analysis, and the like).

EoE Diagnosis

It is well known to medical professionals that early diagnosis of EoE is tremendously beneficial to the patient, as it allows for earlier treatment and better management of symptoms. For example, EoE-induced tissue scarring can occur, with the degree of scarring being related to the duration of disease prior to diagnosis (Schoepfer, A. et al. Gastroenterology 145:1230-6 (2013)). Because many individuals with EoE have the ability to cope with the disease for extended periods of time, for months, years, and even decades, considerable scarring can develop in these patients over this time in addition to the discomfort and loss of quality of life associated with the disease. Such complications over the long-term and short-term can be prevented by early diagnosis.

EoE can be diagnosed by several methods. For example, diagnostic criteria for EoE involving histological analysis of esophageal biopsies have been developed and are widely clinically applied. EoE is defined as peak eosinophil count ≥15 eosinophils/HPF in esophageal biopsy sections in the absence of known causes of esophageal eosinophilia including GERD.

Correlations between EoE and gene expression levels can also provide a basis for conducting a diagnosis of EoE. Such correlations include, but are not limited to, those described in, for example, U.S. Patent Application No. 60/633,909, EOTAXIN-3 IN EOSINOPHILIC ESOPHAGITIS, filed on Dec. 27, 2004; U.S. Pat. No. 8,030,003, DIAGNOSIS OF EOSINOPHILIC ESOPHAGITIS BASED ON PRESENCE OF AN ELEVATED LEVEL OF EOTAXIN-3, issued Oct. 4, 2011 and filed as U.S. patent application Ser. No. 11/721,127 on Jun. 7, 2007; U.S. patent application Ser. No. 12/492,456, EVALUATION OF EOSINOPHILIC ESOPHAGITIS, filed on Jun. 26, 2009; U.S. patent application Ser. No. 12/628,992, IL-13 INDUCED GENE SIGNATURE FOR EOSINOPHILIC ESOPHAGITIS, filed on Dec. 1, 2009; U.S. Provisional Application No. 61/430,453, A STRIKING LOCAL ESOPHAGEAL CYTOKINE EXPRESSION PROFILE IN EOSINOPHILIC ESOPHAGITIS, filed on Jan. 6, 2011; U.S. patent application Ser. No. 13/051,873, METHODS AND COMPOSITIONS FOR MITIGATING EOSINOPHILIC ESOPHAGITIS BY MODULATING LEVELS AND ACTIVITY OF EOTAXIN-3, filed on Mar. 18, 2011; U.S. patent application Ser. No. 13/132,884, DETERMINATION OF EOSINOPHILIC ESOPHAGITIS, filed on Jun. 3, 2011; U.S. Provisional Application No. 61/497,796, NEGATIVE REGULATION OF EOSINOPHIL PRODUCTION BY TOLL-LIKE RECEPTORS, filed on Jun. 16, 2011; U.S. Patent Application No. 61/571,115, DIAGNOSTIC METHODS OF EOSINOPHILIC ESOPHAGITIS, filed on Jun. 21, 2011; U.S. Provisional Application No. 61/500,508, MOLECULAR DIAGNOSTIC PANEL OF EOSINOPHILIC GASTROINTESTINAL DISORDERS, filed on Jun. 23, 2011; U.S. patent application Ser. No. 13/132,295, METHODS OF DETERMINING EFFICACY OF GLUCOCORTICOID TREATMENT OF EOSINOPHILIC ESOPHAGITIS, filed on Aug. 22, 2011; PCT Patent Application No. US2012/020556, ESOPHAGEAL CYTOKINE EXPRESSION PROFILES IN EOSINOPHILIC ESOPHAGITIS, filed on Jan. 6, 2012; U.S. Provisional Application No. 61/602,897, ESOPHAGEAL MICRORNA EXPRESSION PROFILES IN EOSINOPHILIC ESOPHAGITIS, filed on Feb. 24, 2012; PCT Patent Application No. US2012/42985, BLOCKADE OF EOSINOPHIL PRODUCTION BY TOLL-LIKE RECEPTORS, filed on Jun. 18, 2012; PCT Patent Application No. US2012/043640, DIAGNOSTIC METHODS FOR EOSINOPHILIC ESOPHAGITIS, filed on Jun. 21, 2012; PCT Patent Application No. US2012/044061, MOLECULAR DIAGNOSTIC PANEL OF EOSINOPHILIC GASTROINTESTINAL DISORDERS, filed on Jun. 25, 2012; PCT Patent Application No. US2013/27503, ESOPHAGEAL MICRORNA EXPRESSION PROFILES IN EOSINOPHILIC ESOPHAGITIS, filed on Feb. 23, 2013; U.S. patent application Ser. No. 13/978,117, ESOPHAGEAL CYTOKINE EXPRESSION PROFILES IN EOSINOPHILIC ESOPHAGITIS, filed on Jul. 2, 2013; U.S. patent application No. TBD, BLOCKADE OF EOSINOPHIL PRODUCTION BY TOLL-LIKE RECEPTORS, filed on Dec. 13, 2013; U.S. patent application No. TBD, DIAGNOSTIC METHODS FOR EOSINOPHILIC ESOPHAGITIS, filed on Dec. 20, 2013; and U.S. patent application Ser. No. 14/128,887, MOLECULAR DIAGNOSTIC PANEL OF EOSINOPHILIC GASTROINTESTINAL DISORDERS, filed on Dec. 23, 2013. In addition, the measurement of CAPN14 expression as described herein can be used in EoE diagnostic and monitoring tests. For example, EoE diagnostic panels based on the EoE transcriptome have been described. Some embodiments of the present invention involve the use of such diagnostic panels.

EoE Therapies

The treatment of EoE is distinct from other forms of esophagitis, as effective management depends upon elimination of the triggering food types or the usage of anti-inflammatory medications (e.g. glucocorticoids). Accordingly, it is important to differentiate EoE from other gastrointestinal afflictions, such as gastroesophageal reflux disease (GERD).

Certain embodiments of the invention involve administering EoE therapies, including allergen removal, steroid treatment, dietary management, the combination of steroid treatment and dietary management, the use of food allergen skin patches, and the use of proton pump inhibitors (PPIs). EoE therapies also include administration of topical glucocorticoids, such as fluticasone, budesonide, or ciclesonide, humanized antibodies against relevant cytokines and/or mediators, such as eotaxin-1, eotaxin-3, IL-13, IL-5, IL-5Rα, CD49D, SIGLEC-8, IgE, CD300A, TSLP, and/or IL-33, small molecule inhibitors of an eosinophil and/or allergic disease activation pathway, such as a notch-signaling inhibitor or an inhibitor or antagonist of CCR3, CCL11, CCL26, VLA4, CRTH2, KRT23, COL1A2, and COL8A2 prostaglandin D2, histamine H4 receptor, IL-13, IL-4, and/or the common β chain. Such treatments can be swallowed or systemic.

In some embodiments, EoE can be treated through the blockade of eosinophil recruitment, such as through CCR3 and/or CCL11 inhibition, adhesion molecule inhibition, CRTH2 and prostaglandin D2 inhibition, histamine H4 receptor inhibition, IL-13 and/or IL-4 blockade, and the like. Compounds that can be used for these purposes include, for example, small molecule CCR3 antagonists and/or eotaxin-1-specific antibodies for CCR3 and/or CCL11 inhibition, CD49D-specific antibodies and/or small molecule VLA4 antagonists for adhesion molecule inhibition, CRTH2 antagonists for CRTH2 and prostaglandin D2 inhibition, small molecule histamine H4 receptor antagonists for histamine H4 receptor inhibition, and IL-13-specific antibodies, IL-4Rα antagonists, IL-4 variants for IL-13 and/or IL-4 blockade, and the like. Specific examples of such compounds include, for example, small molecule CCR3 antagonists, such as LH31407, eotaxin-1-specific antibodies, such as bertilimumab, CD49D-specific antibodies, such as natalizubam, small molecule VLA4 antagonists, such as compound 1, CRTH2 antagonists, such as Ser. No. 00/000,459, small molecule histamine H4 receptor antagonists, such as INCB38579, IL-13-specific antibodies, such as lebrikizumab, IL-4Rα antagonists, such as dupilumab and AMG 317, IL-4 variants, such as pitrakinra, and the like.

In some embodiments, EoE can be treated through the inhibition of eosinophil survival, such as through IL-5 and/or IL-5Rα blockade, SIGLEC-8 antagonism, IgE blockade, activation of inhibitory receptors, TSLP inhibition, and the like. Compounds that can be used for these purposes include, for example, IL-5-specific antibodies, IL-5Rα-specific antibodies, and/or antisense oligonucleotides directed against the common β chain for IL-5 and/or IL-5Rα blockade, SIGLEC-8-specific antibodies for SIGLEC-8 antagonism, IgE-specific antibodies for IgE blockade, CD300A-specific antibodies for activation of inhibitory receptors, TSLP-specific antibodies for TSLP inhibition, and the like. Specific examples of such compounds include, for example, IL-5-specific antibodies, such as mepolizumab and reslizumab, IL-5Rα-specific antibodies, such as benralizumab, antisense oligonucleotides directed against the common β chain, such as TPI ASM8, SIGLEC-8-specific antibodies, IgE-specific antibodies, such as omalizumab, CD300A-specific antibodies, TSLP-specific antibodies, such as AMG 157, and the like.

In some embodiments, EoE can be treated through the inhibition of eosinophil activation, such as through IL-33 blockade, notch inhibition, and the like. Compounds that can be used for these purposes include, for example, IL-33-specific antibodies for IL-33 blockade, notch signaling inhibitors for notch inhibition, and the like. Specific examples of such compounds include, for example, IL-33-specific antibodies, notch signaling inhibitors, such as semagacestat, and the like.

In some embodiments, EoE can be treated through the blockade of eosinophil production, such as through IL-5R blockade, and the like. Compounds that can be used for these purposes include, for example, IL-5Rα-specific antibodies for IL-5R blockade, and the like. Specific examples of such compounds include, for example, IL-5Rα-specific antibodies, such as benralizumab, and the like.

The example targeting strategies and compounds presently provided are intended to be representative. One of skill in the art will recognize that different compounds from those listed above can be used to achieve a comparable outcome and how to identify such compounds.

Heretofore unknown therapeutics can be developed by the screening of various compounds. Compounds that can be screened to determine their utility as EoE therapeutics include for example, but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular libraries made of D- or L-configuration amino acids, or both, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')2 and Fab expression library fragments, and epitope-binding fragments thereof), organic and inorganic molecules, and the like.

In addition to the more traditional sources of test compounds, computer modeling and searching technologies permit the rational selection of test compounds by utilizing structural information from the ligand binding sites relevant proteins. Such rational selection of test compounds can decrease the number of test compounds that must be screened in order to identify a therapeutic compound. Knowledge of the sequences of relevant proteins allows for the generation of models of their binding sites that can be used to screen for potential ligands. This process can be accomplished in several manners known in the art. A preferred approach involves generating a sequence alignment of the protein sequence to a template (derived from the crystal structures or NMR-based model of a similar protein(s), conversion of the amino acid structures and refining the model by molecular mechanics and visual examination. If a strong sequence alignment cannot be obtained then a model can also be generated by building models of the hydrophobic helices. Mutational data that point towards residue-residue contacts can also be used to position the helices relative to each other so that these contacts are achieved. During this process, docking of the known ligands into the binding site cavity within the helices can also be used to help position the helices by developing interactions that would stabilize the binding of the ligand. The model can be completed by refinement using molecular mechanics and loop building using standard homology modeling techniques. (General information regarding modeling can be found in Schoneberg, T. et. al. *Molecular and Cellular Endocrinology* 151:181-93 (1999); Flower, D. *Biochimica et Biophysica Acta* 1422:207-34 (1999); and Sexton, P. *Current Opinion in Drug Discovery and Development* 2:440-8 (1999).)

Once the model is completed, it can be used in conjunction with one of several existing computer programs to narrow the number of compounds to be screened by the screening methods of the present invention, like the DOCK program (UCSF Molecular Design Institute, San Francisco, Calif.). In several of its variants it can screen databases of commercial and/or proprietary compounds for steric fit and rough electrostatic complementarity to the binding site. Another program that can be used is FLEXX (Tripos Inc., St. Louis, Mo.).

Administration

Compounds used as therapeutic targets or agents can be administered via oral or parenteral delivery routes (subcutaneous or intravenous), as has been described previously (van Rooij, E. et al. Circ. Res. 110:496-507 (2012)). Such therapeutics can be administered by any pharmaceutically acceptable carrier, including, for example, any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional medium or agent is incompatible with the active compound, such media can be used in the compositions of the invention. Supplementary active compounds can also be incorporated into the compositions. A pharmaceutical composition of the invention is formulated to be compatible with its intended route of administration. Routes of administration include for example, but are not limited to, intravenous, intramuscular, and oral, and the like. Additional routes of administration include, for example, sublingual, buccal, parenteral (including, for example, subcutaneous, intramuscular, intraarterial, intradermal, intraperitoneal, intracisternal, intravesical, intrathecal, or intravenous), transdermal, oral, transmucosal, and rectal administration, and the like.

Solutions or suspensions used for appropriate routes of administration, including, for example, but not limited to parenteral, intradermal, or subcutaneous application, and the like, can include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose, and the like. The pH can be adjusted with acids or bases, such as, for example, hydrochloric acid or sodium hydroxide, and the like. The parenteral preparation can be enclosed in, for example, ampules, disposable syringes, or multiple dose vials made of glass or plastic, and the like.

Pharmaceutical compositions suitable for injectable use include, for example, sterile aqueous solutions (where water soluble) or dispersions and sterile powders for the extemporaneous preparation of sterile injectable solutions or dispersion, and the like. For intravenous administration, suitable carriers include, for example, physiological saline, bacteriostatic water, Cremophor EL™ (BASF, Parsippany, N.J.) or phosphate buffered saline (PBS), and the like. In all cases, the composition should be fluid to the extent that easy syringability exists. The carrier can be a solvent or dispersion medium containing, for example, water, ethanol, polyol (for example, glycerol, propylene glycol, and liquid polyethylene glycol, and the like), and suitable mixtures thereof, and the like. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, such as, for example, parabens, chlorobutanol, phenol, ascorbic acid, thimerosal, and the like. In many cases, it can be preferable to include isotonic agents, such as, for example, sugars, polyalcohols such as mannitol, sorbitol, and sodium chloride, and the like, in the composition. Prolonged absorption of the injectable compositions can be brought about by including in the composition an agent which delays absorption such as, for example, aluminum monostearate and gelatin, and the like.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets, for example. For oral administration, the agent can be contained in enteric forms to survive the stomach or further coated or mixed to be released in a particular region of the gastrointestinal (GI) tract by known methods. For the purpose of oral therapeutic administration, the active compound can be incorporated with excipients and used in the form of tablets, troches, or capsules, or the like. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following exemplary ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate; a glidant such as colloidal silicon dioxide; a sweetening agent such as sucrose or saccharin; or a flavoring agent such as peppermint, methyl salicylate, or orange flavoring, or the like.

For administration by inhalation, the compounds can be delivered in the form of an aerosol spray from pressured container or dispenser, which contains a suitable propellant, e.g., a gas such as carbon dioxide, or a nebulizer, or the like.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives, and the like. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems, and the like. Biodegradable, biocompatible polymers can be used, such as, for example, ethylene vinyl acetate, polyanhydrides, polyglycolic acid, collagen, polyorthoesters, and polylactic acid, and the like. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference in its entirety.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The details for the dosage unit forms of the invention are dictated by and directly dependent on the unique characteristics of the active compound and the particular therapeutic effect to be achieved, and the limitations inherent in the art of compounding such an active compound for the treatment of individuals. Such details are known to those of skill in the art.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of subjects with a positive test result who are correctly diagnosed; for tests with a high PPV, a positive test indicates the presence of the condition in question. The NPV of a particular diagnostic test represents the proportion of subjects with a negative test result who are correctly diagnosed; for tests with a high NPV, a negative test indicates the absence of the condition. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition.

The disclosure, figures, and tables herein make mention of statistical significance and "p values." While p values below 0.05 are considered to be statistically significant, it is within the scope of embodiments of the present invention to make use of correlations having a reported p value above 0.05 as well as below 0.05. For example, in a study having a small sample size but a genuine correlation, a p value can be above 0.05, such as, for example, 0.06, 0.07, 0.08, 0.09, 0.10, 0.15, or more. Since p value is affected by sample size, two studies can have the same proportion of outcomes, and a study with a smaller sample size can have a p value above 0.05, while the study with the larger sample size can have a p value below 0.05, even though the correlation is proportionally the same. Thus, while a p value below 0.05, for any sample size, is a strong indication of a statistically significant correlation, a genuine correlation can exist, that is tested with a small sample size, and the p value of such a test can be above 0.05.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Study Population

Subjects

The study was approved by the Institutional Review Boards at Cincinnati Children's Hospital Medical Center (CCHMC) and all participating sites that were part of the NIH Consortium of Food Allergy Research EoE Cohort (Mount Sinai Medical Center, University of North Carolina, Johns Hopkin's University, University of Colorado Health Center/National Jewish Research Center, and Arkansas Children's Hospital). Parental informed consent was obtained from all participants in this study for the purpose of DNA collection and genotyping.

Cases were confirmed by a physician to fulfill the diagnostic criteria for EoE. EoE is defined as peak eosinophil count ≥15 eosinophils/high-power field in esophageal biopsy sections; 30% of CCHMC and 51% of CoFAR patients had PPI therapy before the diagnostic endoscopy. Control subjects (non-EoE) included the self-reported Caucasian subjects in the Cincinnati Genomic Control Cohort CCHMC (n=831, age range 2-18 years) (Prahalad, S. et al. *Arthritis Rheum* 43:2335-8 (2000)) and an external control cohort (non-EoE) acquired from a database of Genotypes and Phenotypes (dbGAP) University of Michigan study (n=8,580). In the CCHMC and CoFAR cohorts, 73% and 62% of EoE patients were male, respectively, and EoE patients had an age range of 2-52 years. The external control cohort was collected through an aging and retirement study; these subjects were significantly older than the cases at the time of DNA collection. The subjects in the external control cohort were randomly assigned to the Discovery or Replication analysis with the goal of equivalent case:control ratios in each cohort.

Population Stratification

Genome-wide data were used to infer the top six principal components of genetic variation and correct for possible population stratification using Eigensoft. All local cases and controls were self-identified as having European ancestry, and principal component analysis was used to exclude all subjects (n=271) who segregated more than 4 standard deviations outside of the mean of the first 4 principal components. Specifically, 34 genetic outliers were removed from 736 EoE cases, 13 from 235 CoFAR cases, 71 of 831 CCHMC controls, and 166 of 8,652 dbGAP University of Michigan controls. The resulting genomic inflation factor was 1.001 in a set of ancestral informative markers not including the associated loci.

Example 2

Genotyping

Genotyping

Genotyping was performed on the Illumina OMNI-5 and OMNI-2.5 genotyping arrays (Illumina, San Diego, Calif.) using Infinium2 chemistry. Genotypes were called using the Gentrain2 algorithm within Illumina Genome Studio.

Genotyping Quality Control

Figure 15:
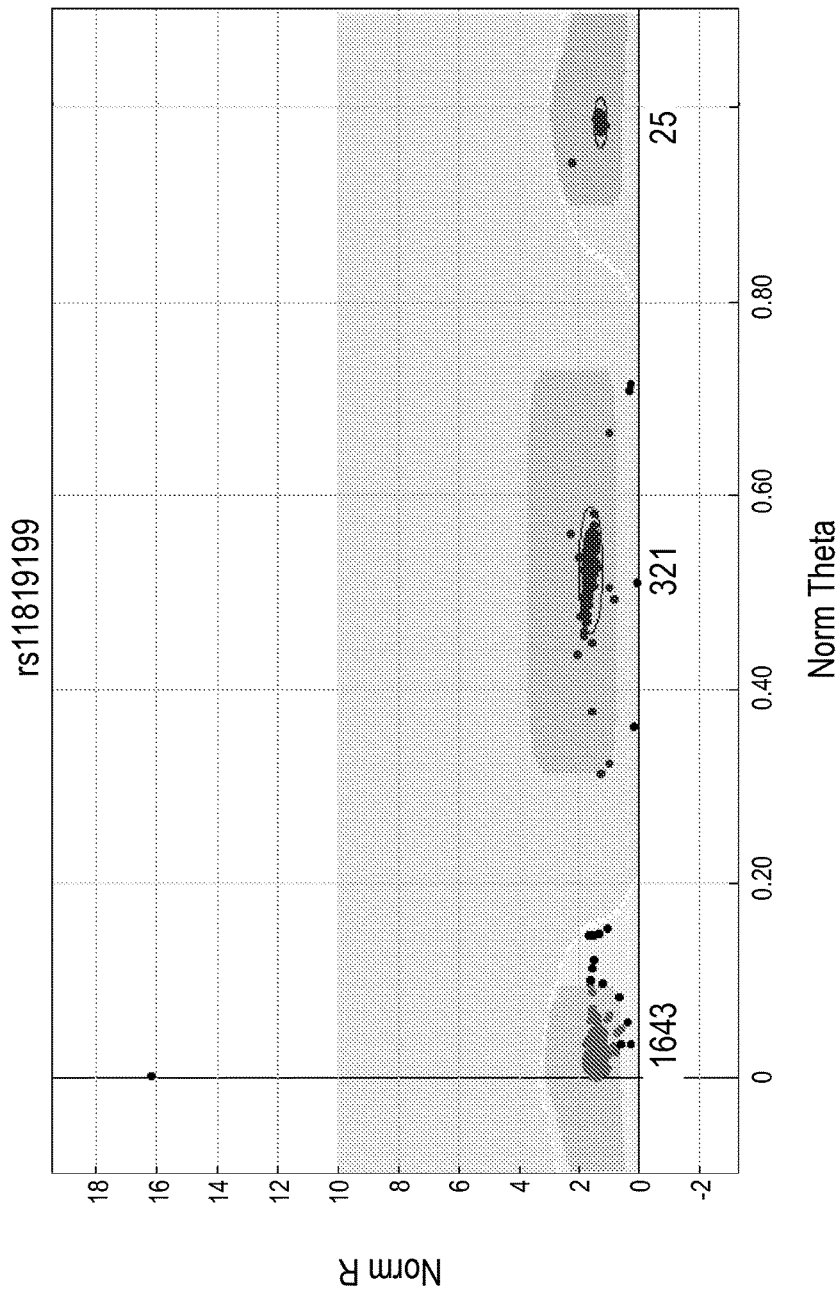
FIG. 15. The Genome-Studio cluster plot for rs11819199 at 15q13 on chromosome 15 from the OMNI5 analysis (all EoE cases and local controls). The normalized theta (Norm Theta) is the ratio of signal intensities assayed for the A and B of the rs11819199 allele against normalized R (signal intensity; Norm R). Subjects in this graph are homozygous risk (left-hand group), heterozygotes (center group), or homozygous non-risk (right-hand group).

To confirm accurate genotyping and sample identification, an identity-by-state analysis was performed on a subset of 10,732 SNPs that were genotyped on both the Illumina OMNI-5 and the previous GWAS platform (Illumina 550) (Rothenberg, M. E. et al. Nat Genet 42:289-91 (2010)); this analysis found 99.998% concordance between the 134 samples that were genotyped on both platforms. Of the original 4,301,332 markers on the OMNI-5, 2,512,766 were derived from rare variants (<1% MAF). Notably, 87,539 markers had a suboptimal call rate (e.g. <96%), 44,246 were not in Hardy Weinberg Equilibrium in the controls ($p<10^{-4}$), and upon visual inspection, 124 SNPs did not cluster properly. The rs11819199 SNP reached genome-wide significance; however, no other SNPs around this variant in the dataset were strongly associated. The Genome-Studio cluster plot of this particular SNP is given in FIG. 15. External controls were genotyped on the OMNI-2.5, and overlapping variants that passed the quality measures described above in both datasets were analyzed. The final genotyping rate for all SNPs was 99.7%. After applying the above filters, genotypes were used from 1,468,075 autosomal SNPs in a discovery cohort of 435 cases and 716 well phenotyped local controls from CCHMC and 5,776 controls from the dbGAP study and a replication cohort of 222 cases from the NIH CoFAR EoE cohort and 2,804 controls from the University of Michigan Health and Retirement System (obtained from dbGAP) (Table 1).

TABLE 1

Subjects in the EoE GWAS.

| | Local EoE cohort | | External CoFAR EoE | | Local controls | | External University of Michigan controls | |
|---|---|---|---|---|---|---|---|---|
| | Males | Females | Males | Females | Males | Females | Males | Females |
| Discovery cohort | 376 | 138 | | | 376 | 384 | 2,459 | 3,539 |
| Replication cohort | | | 150 | 72 | | | 1,020 | 1,468 |
| Combined analysis | 514 | | 222 | | 760 | | 8,486 | |

Association and Linkage Disequilibrium Analysis

After removing genetic outliers, a logistic regression was performed to calculate p values and odds ratios for each SNP using PLINK (Purcell, S. et al. Am J Hum Genet 81:559-75 (2007)) with gender as a co-variant. For some analyses, atopy and the most significant SNP in the region were also used as covariates. For analyses that used atopy as a covariate, only subjects with known atopic status (EoE cases and local Cincinnati controls) were included. For cases, atopy was defined by a physician-documented history of positive skin-prick test, allergic rhinitis, allergic dermatitis/eczema, asthma, or food allergy. The prevalence of atopy for the local CCHMC and CoFAR EoE cohorts were 96.2 and 91.3%, respectively. For the Cincinnati Genomic Control Cohort, atopy was defined as parent-reported history of allergic rhinitis, eczema, asthma, or food allergy; the atopy prevalence of this cohort was 28.6%. LocusZoom (Pruim, R. J. et al. Bioinformatics 26:2336-7 (2010)) and R were used to map the associated loci in the context of chromosomal recombination and nearby genes.

Imputation to the 1.000 Genomes Reference Panel

To detect associated variants that were not directly genotyped, highly associated regions were imputed with IMPUTE2, and a composite imputation reference panel of integrated haplotypes was used from the 1,000 Genomes Project sequence data freezes from March 2012 produced using SHAPIT2 (Marchini, J. et al. Nat Genet 39:906-13 (2007); Altshuler, D. M. et al. Nature 467:52-8 (2010); The 1000 Genomes Project Consortium Nature 467:1061-73 (2010)). Imputed genotypes were required to meet or exceed a probability threshold of 0.9, an information measure of >0.4, and the same quality-control criteria threshold described for the genotyped markers.

Example 3

RNA Analyses

Expression Analysis

Quantitative real-time PCR analysis was performed on cDNA from distal esophageal biopsy RNA. EoE biopsies showed active disease pathology at the time when they were taken, and all patients reported no glucocorticoid treatment at the time of biopsy, except for the analysis of gene expression as a function of disease activity in which remission was defined after glucocorticoid therapy. Statistical testing for mRNA expression normalized to glyceraldehyde 3-phosphate dehydrogenase (GAPDH) was determined by Mann-Whitney U test using GraphPad Prism software.

Expression Microarray Analysis

For each patient, one distal esophageal mucosal biopsy sample was immersed in RNAlater RNA stabilization reagent (QIAGEN, Venlo, Limberg, Netherlands) and stored at 4° C. for less than 15 days. Total RNA was extracted using RNeasy Mini Kit (QIAGEN) according to the manufacturer's recommendations. Hybridization to DNA microarray was performed by the Microarray Core at CCHMC, as previously reported (Zimmermann, N. et al. J Clin Invest 111:1863-74 (2003); Blanchard, C. et al. J Clin Invest 116:536-47 (2006)). The genome-wide human Affymetrix U133 Plus 2.0 GeneChip was used, and gene transcript levels were determined using algorithms in the Microarray Analysis Suite and GeneSpring software (Silicon Genetics).

RNA Sequencing

Esophageal biopsy RNA was isolated from EoE patients with active disease and unaffected controls as previously described (Blanchard, C. et al. J Clin Invest 116:536-47 (2006)). RNA sequencing acquiring 10 million mappable 100 base-pair reads from paired-end libraries was performed at the Genetic Variation and Gene Discovery Core Facility at CCHMC. Data were aligned to the GrCh37 build of the human genome using the Ensembl (Flicek, P. et al. *Nucleic Acids Res* 41:D48-55 (2013)) annotations as a guide for TopHat (Trapnell, C. et al. *Bioinformatics* 25:1105-11 (2009)). Expression analysis was performed using Cufflinks (Trapnell, C. et al. *Nat Biotechnol* 28:511-5 (2010)). Data were visualized using the Integrative Genomics Viewer (Broad Institute, Cambridge, Mass.).

Electrophoretic Mobility Shift Assay (EMSA)

Pairs of single stranded 5' IRDye infrared dye labeled and unlabeled oligonucleotides (obtained from IDT Inc, Coralville, Iowa, USA) were annealed to generate double stranded probes. Twenty-five to fifty fmoles of labeled probes was incubated with 8 or 10 µg of nuclear extract prepared from esophageal cell line TE-7, 6 ug poly (deoxyinosinic-doxycytidylic) acid, and 1 µl salmon sperm provided along with the buffers and protocols supplied with the Odyssey Infrared EMSA kit (LI-COR Biosciences, Lincoln, Nebr., USA). The binding reactions were analyzed using electrophoresis on 6% tris-borate-EDTA polyacrylamide gels and detected by an infrared fluorescent procedure using the Odyssey Infrared Imaging System (LI-COR Biosciences, Lincoln, Nebr., USA).

Example 4

Cell Culture and Analysis

Organotropic Cultures

For the air-liquid interface (ALI) culture system, the esophageal epithelial cell line (hTERT-immortalized EPC2 line from Dr. Anil Rustgi of the University of Pennsylvania) was grown to confluence on 0.4 µm pore-size polyester permeable supports (Corning Incorporated, Corning, N.Y., USA) in keratinocyte serum-free media (K-SFM) (Life Technologies, Grand Island, N.Y., USA) supplemented with 1.8 mM calcium. Epithelial differentiation was then induced by removing culture media from the inner chamber of the permeable support and maintaining the esophageal epithelial cells for 5-7 days at the ALI in the presence or absence of IL-13 (100 ng/mL).

H3K27Ac Analysis

Ten to twenty million TE-7 cells were fixed with 0.8% formaldehyde by adding 1 ml of 10× fixation buffer (50 mM Hepes-KOH, pH 7.5, 100 mM NaCl, 1 mM EDTA, 0.5 mM EGTA, 8% formaldehyde) to 9 ml of growth medium for 8 minutes at room temperature with shaking. The reaction was stopped by adding glycine to a final concentration of 125 mM for an additional 5 minutes. Nuclei were prepared with truChIP™ High Cell Chromatin Shearing Kit with SDS Shearing Buffer (Covaris, Woburn, Mass., USA) according to manufacturer recommendations. Sonication was performed using a Covaris S220 Focused ultrasonicator at 175 pip, 10% output, 200 bursts for 8 minutes. Efficient DNA fragmentation was verified by agarose gel electrophoresis. ChIP was performed with 2 ug of H3K27Ac antibody (ab4729, Abcam) in SX-8G IP-Start Automated System (Diagenode, Denville, N.J., USA) in RIPA buffer (TE+0.1% SDS, 1% Triton X-100, 150 mM NaCl, 0.1% sodium deoxycholate) following the protocol of the manufacturer. Fastq files from Illumina pipeline were aligned by bowtie (version 1.0.0) (Langmead, B. et al. *Genome Biol* 10:R25 (2009)), and unique reads were identified with no more than one error allowed for alignment. MACS2 (version 2.0.10.20130712) (Zhang, Y. et al. *Genome Biol* 9:R137 (2008)) was used to identify islands of enrichment (q-value threshold less than 0.2) and estimate fragment size. For visualization, data were uploaded to the University of California, Santa Cruz genome browser.

Calpain Activity Assay

EPC2 cultures were treated with or without IL-13 (100 ng/mL) for 48 hours and lysed with MPER lysis buffer (#78501, Pierce, Rockford, Ill., USA) with 1 mM EDTA and 1 mM DTT on ice. Calpain activity was measured with the Promega Calpain-Glo protease assay according to the manufacturer's instructions. Briefly, 50 µl of lysate was incubated for 10 minutes with reaction buffer and +/−60 uM acetyl-calpastatin (#2950, Tocris, Bristol, United Kingdom), and luminescence was read using the Biotek Synergy2 Multi-Mode Microplate reader (Biotek, Winooski, Vt., USA).

Example 5

Results

Figure 2A:
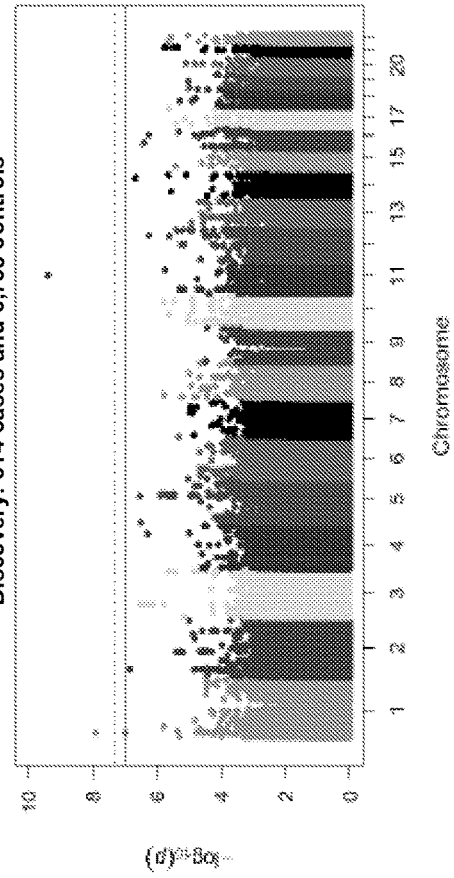
FIG. 2A. Data are from 1,468,075 genetic variants with minor allele frequencies greater than 1% in the subjects with EoE in a discovery cohort of 514 EoE cases and 6,758 controls.
Figure 2B:
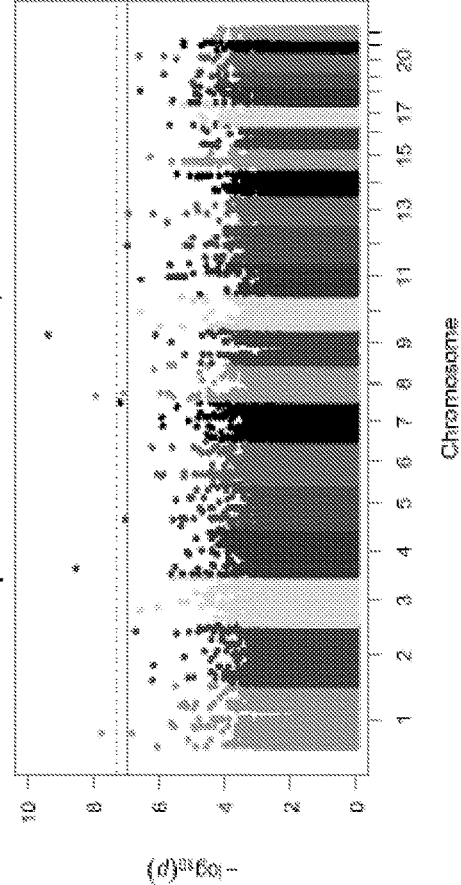
FIG. 2B. Data are from 1,468,075 genetic variants with minor allele frequencies greater than 1% in the subjects with EoE in a replication cohort of 222 cases and 2,488 controls. The −log of the probability is shown as a function of the genomic position of the autosomes. Genome-wide significance (dotted line, $p \leq 5 \times 10^{-8}$) and suggestive significance (solid line, $p \leq 10^{-7}$) are indicated.

Initial genetic association analysis identified 20 SNPs at 17 loci with threshold p-value $<10^{-7}$. Ten of these loci were identified in the discovery cohort ($p<10^{-4}$) and in an analysis in which the external controls were excluded ($p<5\times10^{-2}$), and also independently confirmed in the replication cohort ($p<5\times10^{-2}$; Tables 1-6, FIGS. 1 and 2). Variants were required to demonstrate association ($p<0.05$) in the discovery and replication cohorts, as shown in Table 1, as well as a local cohort analysis including all of the EoE cases in the discovery cohort and the locally recruited controls.

TABLE 2

Most highly associated EoE-risk variants*.

| Chr band | SNP | BP | Minor allele | MAF cases | MAF controls | Major allele | P-value | OR | Nearest Gene | Genomic context |
|---|---|---|---|---|---|---|---|---|---|---|
| 1p13 | rs2000260 | 108673405 | G | 0.37 | 0.43 | A | $6.56 \times 10^{-7}$ | 0.757 | SLC25A24 | |
| 2p23 | rs77569859 | 31411287 | G | 0.09 | 0.05 | A | $\mathbf{3.30 \times 10^{-10}}$ | 1.98 | CAPN14 | intronic |
| 5q22 | rs3806933 | 110406742 | A | 0.37 | 0.44 | G | $\mathbf{2.00 \times 10^{-8}}$ | 0.731 | TSLP | non-coding |
| 5q23 | rs2055376 | 116181428 | A | 0.04 | 0.02 | C | $7.12 \times 10^{-8}$ | 2.3 | near SEMA6a | |
| 8p23 | rs2898261 | 10958539 | A | 0.35 | 0.42 | C | $\mathbf{4.84 \times 10^{-8}}$ | 0.735 | XKR6 | intronic |
| 10p12 | rs11819199 | 20865157 | G | 0.09 | 0.06 | A | $2.89 \times 10^{-7}$ | 1.62 | MIR4675 | |
| 11q13 | rs2155219 | 76299194 | C | 0.413 | 0.491 | A | $3.65 \times 10^{-7}$ | 0.729 | between C11orf30 and LRRC32 | |

TABLE 2-continued

Most highly associated EoE-risk variants*.

| Chr band | SNP | BP | Minor allele | MAF cases | MAF controls | Major allele | P-value | OR | Nearest Gene | Genomic context |
|---|---|---|---|---|---|---|---|---|---|---|
| 11q14 | rs118086209 | 86104495 | C | 0.03 | 0.02 | A | $2.35 \times 10^{-7}$ | 2.19 | CCDC81 | intronic |
| 15q13 | rs8041227 | 31538542 | A | 0.2 | 0.28 | G | $6.34 \times 10^{-10}$ | 0.657 | between LOC283710 and KLF13 | |
| 21q22 | rs17004598 | 45078556 | C | 0.03 | 0.01 | A | $1.37 \times 10^{-7}$ | 2.57 | HSF2BP | intronic |

*The most highly associated variant is shown for each loci.
Chr and band: chromosome and cytogenetic band;
SNP: rs ID of variant;
BP: build 37 map position of the SNP;
MAF: minor allele frequency across cases or controls;
P-value: Fisher's combined P-value for the discovery and replication;
OR: odds ratio for the minor allele;
Nearest gene: spanning or flanking (<1 Mb away from) the index SNP.
Bold font indicates genome-wide significant loci.

TABLE 3

Continuation of Table 2, Most highly associated EoE-risk variants*.

| Chr band | SNP | BP | p-value CCHMC discovery | OR-CCHMC discovery | p-value-CoFAR replication | OR-CoFAR replication |
|---|---|---|---|---|---|---|
| 1p13 | rs2000260 | 108673405 | $1.10 \times 10^{-4}$ | 0.773 | $1.7 \times 10^{-3}$ | 0.725 |
| 2p23 | rs77569859 | 31411287 | $1.41 \times 10^{-7}$ | 1.93 | $1.2 \times 10^{-3}$ | 2.06 |
| 5q22 | rs3806933 | 110406742 | $1.32 \times 10^{-6}$ | 0.724 | $3.1 \times 10^{-3}$ | 0.74 |
| 5q23 | rs2055376 | 116181428 | $1.89 \times 10^{-6}$ | 2.29 | $7.7 \times 10^{-3}$ | 2.4 |
| 8p23 | rs2898261 | 10958539 | $1.73 \times 10^{-6}$ | 0.724 | $6.2 \times 10^{-3}$ | 0.755 |
| 10p12 | rs11819199 | 20865157 | $1.64 \times 10^{-5}$ | 1.62 | $2.00 \times 10^{-3}$ | 1.7 |
| 11q13 | rs2155219 | 76299194 | $2.64 \times 10^{-5}$ | 0.743 | $5.8 \times 10^{-3}$ | 0.699 |
| 11q14 | rs118086209 | 86104495 | $1.93 \times 10^{-4}$ | 1.99 | $6.61 \times 10^{-5}$ | 2.83 |
| 15q13 | rs8041227 | 31538542 | $3.97 \times 10^{-6}$ | 0.693 | $3.38 \times 10^{-5}$ | 0.581 |
| 21q22 | rs17004598 | 45078556 | $4.48 \times 10^{-6}$ | 2.59 | $3.3 \times 10^{-3}$ | 2.75 |

*The most highly associated variant is shown for each loci.
BP: build 37 map position of the SNP;
CCHMC: Cincinnati Children's Hospital Medical Center;
CoFAR: NIH Consortium of Food Allergy Research);
Chr and band: chromosome and cytogenetic band;
MAF: minor allele frequency across cases or controls;
Nearest gene: spanning or flanking (<1 Mb away from) the index SNP;
OR: odds ratio for the minor allele;
p-value: the weighted Z-score method implemented in METAL was used to combine the p-values for the discovery and replication cohorts;
SNP: rs ID of variant..
Bold font indicates genome-wide significant loci.

TABLE 4

Variants that demonstrated association in discovery, replication, and local analyses.

| | | | | | All cases and controls (weighted Z-score combined P) | | Cases from CCHMC and controls from CCHMC and University of Michigan (dbGAP) | |
|---|---|---|---|---|---|---|---|---|
| Chr | SNP | BP | MAF cases | MAF controls | p value | OR | p value CCHMC discovery cohort | OR CCHMC discovery cohort |
| 1 | rs2000260 | 108673405 | 0.37 | 0.43 | $6.56 \times 10^{-7}$ | 0.757 | 0.0001099 | 0.773 |
| 2 | rs77569859 | 31411287 | 0.09 | 0.05 | $3.30 \times 10^{-10}$ | 1.982 | $1.41 \times 10^{-7}$ | 1.93 |
| 5 | rs3806933 | 110406742 | 0.37 | 0.44 | $2.00 \times 10^{-8}$ | 0.731 | $1.32 \times 10^{-6}$ | 0.724 |
| 5 | rs2055376 | 116181428 | 0.04 | 0.02 | $7.12 \times 10^{-8}$ | 2.296 | $1.89 \times 10^{-6}$ | 2.289 |
| 8 | rs2898261 | 10958539 | 0.35 | 0.42 | $4.84 \times 10^{-8}$ | 0.735 | $1.73 \times 10^{-6}$ | 0.724 |
| 10 | rs11819199 | 20865157 | 0.09 | 0.06 | $2.89 \times 10^{-7}$ | 1.62 | $1.64 \times 10^{-5}$ | 1.618 |
| 11 | rs2155219 | 76299194 | 0.413 | 0.491 | $3.65 \times 10^{-7}$ | 0.729 | $2.64 \times 10^{-5}$ | 0.743 |

TABLE 4-continued

Variants that demonstrated association in discovery, replication, and local analyses.

| | | | | | All cases and controls (weighted Z-score combined P) | | Cases from CCHMC and controls from CCHMC and University of Michigan (dbGAP) | |
|---|---|---|---|---|---|---|---|---|
| Chr | SNP | BP | MAF cases | MAF controls | p value | OR | p value CCHMC discovery cohort | OR CCHMC discovery cohort |
| 11 | rs118086209 | 86104495 | 0.03 | 0.02 | $2.35 \times 10^{-7}$ | 2.19 | 0.000193 | 1.993 |
| 15 | rs8041227 | 31538542 | 0.2 | 0.28 | $6.34 \times 10^{-10}$ | 0.657 | $3.97 \times 10^{-6}$ | 0.6932 |
| 21 | rs17004598 | 45078556 | 0.03 | 0.01 | $1.37 \times 10^{-7}$ | 2.566 | $4.48 \times 10^{-6}$ | 2.592 |

BP: build 37 map position of the SNP;
CCHMC: Cincinnati Children's Hospital Medical Center;
CoFAR: NIH Consortium of Food Allergy Research);
Chr and band: chromosome and cytogenetic band;
MAF: minor allele frequency across cases or controls;
OR: odds ratio for the minor allele;
p value: the weighted Z-score method implemented in METAL was used to combine the p values for the discovery and replication cohorts;
SNP: rs ID of variant.

TABLE 5

Continuation of Table 4, Variants that demonstrated association in discovery, replication, and local analyses.

| | | | | | Cases and controls from CCHMC | | Cases from CoFAR and separate controls from University of Michigan (dbGAP) | |
|---|---|---|---|---|---|---|---|---|
| Chr | SNP | BP | MAF cases | MAF controls | p value local | OR local | p value replication | OR replication |
| 1 | rs2000260 | 108673405 | 0.37 | 0.43 | 0.00128 | 0.766 | 0.00171 | 0.724 |
| 2 | rs77569859 | 31411287 | 0.09 | 0.05 | 0.00046 | 1.787 | 0.00124 | 2.055 |
| 5 | rs3806933 | 110406742 | 0.37 | 0.44 | 0.00088 | 0.759 | 0.0031 | 0.74 |
| 5 | rs2055376 | 116181428 | 0.04 | 0.02 | $6.24 \times 10^{-6}$ | 3.323 | 0.00772 | 2.4 |
| 8 | rs2898261 | 10958539 | 0.35 | 0.42 | $1.34 \times 10^{-5}$ | 0.696 | 0.00616 | 0.755 |
| 10 | rs11819199 | 20865157 | 0.09 | 0.06 | 0.00032 | 1.735 | 0.00204 | 1.7 |
| 11 | rs2155219 | 76299194 | 0.413 | 0.491 | 0.0005 | 0.742 | 0.00583 | 0.67 |
| 11 | rs118086209 | 86104495 | 0.03 | 0.02 | 0.00106 | 2.479 | $6.61 \times 10^{-5}$ | 2.831 |
| 15 | rs8041227 | 31538542 | 0.2 | 0.28 | 0.00277 | 0.749 | $3.38 \times 10^{-5}$ | 0.581 |
| 21 | rs17004598 | 45078556 | 0.03 | 0.01 | 0.00204 | 2.64 | 0.00329 | 2.754 |

BP: build 37 map position of the SNP;
CCHMC: Cincinnati Children's Hospital Medical Center;
CoFAR: NIH Consortium of Food Allergy Research);
Chr and band: chromosome and cytogenetic band;
MAF: minor allele frequency across cases or controls;
OR: odds ratio for the minor allele;
p value: the weighted Z-score method implemented in METAL was used to combine the p values for the discovery and replication cohorts;
SNP: rs ID of variant.

TABLE 6

Variants that failed to demonstrate association in discovery, replication, or local analyses.

| | | | | | All cases and controls | | Cases from CCHMC and controls from CCHMC and U of Mich (dbGAP) | | Cases and controls from CCHMC | | Cases from CoFAR and separate controls from U of Mich (dbGAP) | |
|---|---|---|---|---|---|---|---|---|---|---|---|---|
| | | | | | (Fisher's combined P) | | P-CCHMC | OR-CCHMC | | | | |
| Chr | SNP | BP | MAF cases | MAF Controls | P-value | Odds Ratio | discovery cohort | discovery cohort | P-local | OR-local | P-replication | OR-replication |
| 1 | rs28530674 | 19234134 | 0.07 | 0.04 | $3.43 \times 10^{-7}$ | 1.826 | $1.24 \times 10^{-8}$ | 2.074 | $6.58 \times 10^{-5}$ | 2.015 | 0.73 | 1.112 |
| 1 | rs2296225 | 21031042 | 0.13 | 0.08 | $1.08 \times 10^{-7}$ | 1.626 | $1.03 \times 10^{-7}$ | 1.713 | 0.0018 | 1.505 | 0.32 | 1.24 |
| 11 | rs77301713 | 76832446 | 0.04 | 0.02 | $1.46 \times 10^{-7}$ | 2.22 | $4.06 \times 10^{-10}$ | 2.669 | $1.72 \times 10^{-5}$ | 2.766 | 0.38 | 0.602 |

TABLE 6-continued

Variants that failed to demonstrate association in discovery, replication, or local analyses.

| | | | | | All cases and controls | | Cases from CCHMC and controls from CCHMC and U of Mich (dbGAP) | | | | Cases from CoFAR and separate controls | |
|---|---|---|---|---|---|---|---|---|---|---|---|---|
| | | | | | (Fisher's combined P) | | P-CCHMC | OR-CCHMC | Cases and controls from CCHMC | | from U of Mich (dbGAP) | |
| Chr | SNP | BP | MAF cases | MAF Controls | P-value | Odds Ratio | discovery cohort | discovery cohort | P-local | OR-local | P-replication | OR-replication |
| 17 | rs3744790 | 76893135 | 0.14 | 0.2 | $8.16 \times 10^{-7}$ | 0.651 | $2.50 \times 10^{-6}$ | 0.623 | $2.58 \times 10^{-5}$ | 0.609 | 0.097 | 0.748 |
| 22 | rs2075277 | 21382482 | 0.13 | 0.09 | $9.36 \times 10^{-7}$ | 1.544 | $2.28 \times 10^{-6}$ | 1.599 | 0.0011 | 1.526 | 0.089 | 1.39 |
| 1 | rs11206830 | 56960123 | 0.04 | 0.02 | $7.92 \times 10^{-8}$ | 2.162 | 0.0017 | 1.775 | 0.18 | 1.377 | $1.49 \times 10^{-7}$ | 3.36 |
| 18 | rs9956738 | 49940973 | 0.03 | 0.01 | $3.53 \times 10^{-7}$ | 2.472 | 0.0038 | 1.913 | 0.11 | 1.613 | $2.59 \times 10^{-7}$ | 4.321 |

BP: build 37 map position of the SNP;
CCHMC: Cincinnati Children's Hospital Medical Center;
CoFAR: NIH Consortium of Food Allergy Research);
Chr and band: chromosome and cytogenetic band;
MAF: minor allele frequency across cases or controls;
OR: odds ratio for the minor allele;
p value: the weighted Z-score method implemented in METAL was used to combine the p values for the discovery and replication cohorts;
SNP: rs ID of variant.

Figure 3:
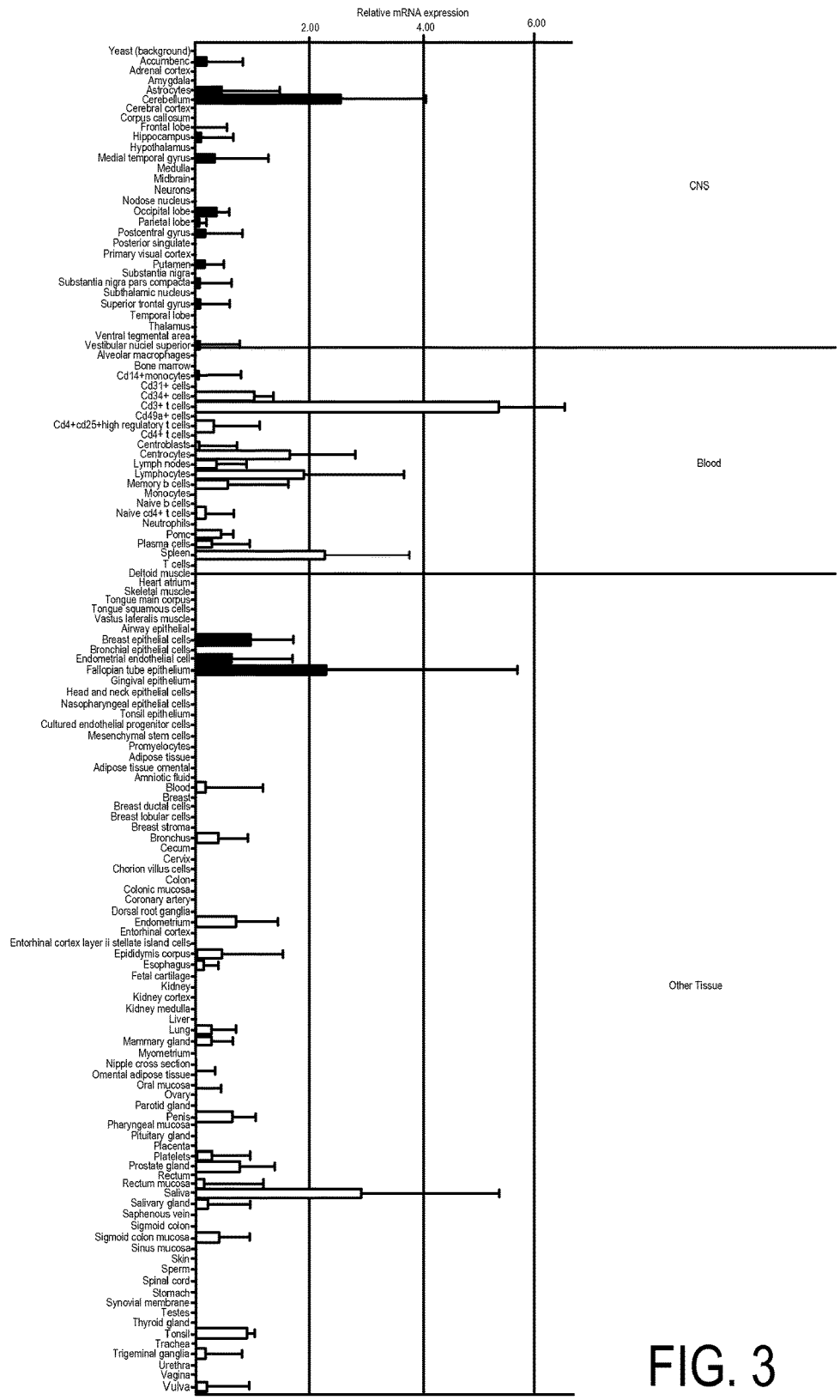
FIG. 3. The expression of XKR6. (data collected form www <dot> biogps <dot> org). The expression is grouped by tissue source, as indicated on the figure.

Markers in 2p23, 5q22, 8p23, and 15q13 reached genome-wide significance ($p<5\times10^{-8}$). The variants most highly associated with increased risk of EoE were found at 2p23 spanning the CAPN14 gene (the best SNP was rs77569859, $p=3.30\times10^{-10}$ odds ratio (OR)=1.98) (Tables 2-3). In order to identify the commonly-occurring variants (minor allele frequency (MAF)>1%) on the risk haplotype that could be driving the genetic association, this region was imputed to a composite reference panel from 1,000 genomes (Marchini, J. et al. *Nat Genet* 39:906-13 (2007); Altshuler, D. M. et al. *Nature* 467:52-8 (2010)); no haplotype of continuous SNPs or haplotype constructed using the most associated variants in the region was more highly associated with EoE risk than rs77569859 alone (the best haplotype had $p=3.5\times10^{-8}$, OR=1.6, FIG. 1B). Variants at the other two newly discovered loci reaching genome-wide significance were located at the XKR6 (XK, Kell blood group complex subunit-related family, member 6) gene (8p23) and in a gene desert (15q13). Very little is known about XKR6; however, public expression databases report expression in the immune compartment (FIG. 3). These four genome-wide susceptibility loci remained associated with EoE, and the effect size was not significantly influenced after correcting for atopy (Table 7).

TABLE 7

Association of the top, replicated loci in a logistic regression adjusted for atopy using all cases (n = 736) and local controls (n = 760).

| Chr | SNP | BP | Band | Nearest Gene | p-value | Odds Ratio | Difference in OR |
|---|---|---|---|---|---|---|---|
| 1 | rs2000260 | 108673405 | 1p13 | SLC25A24 | $7.27 \times 10^{-4}$ | 0.7555 | 0.002 |
| 2 | rs77569859 | 31411287 | 2p23 | CAPN14 | $\mathbf{3.10 \times 10^{-4}}$ | 1.979 | 0.003 |
| 5 | rs3806933 | 110406742 | 5q22 | TSLP/WDR36 | $\mathbf{4.98 \times 10^{-5}}$ | 0.7116 | 0.019 |
| 5 | rs2055376 | 116181428 | 5q23 | Near SEMA6a | $5.56 \times 10^{-3}$ | 2.236 | 0.06 |
| 8 | rs2898261 | 5001364 | 8p23 | XKR6 | $\mathbf{6.23 \times 10^{-2}}$ | 1.401 | -0.666 |
| 10 | rs11819199 | 139337546 | 10p12 | MIR4675 | $3.39 \times 10^{-5}$ | 2.536 | -0.916 |
| 11 | rs2155219 | 20865157 | 11q13 | Between C11orf30 and LRRC32 | $2.95 \times 10^{-4}$ | 1.768 | -1.039 |
| 11 | rs118086209 | 86104495 | 11q14 | CCDC81 | $1.36 \times 10^{-3}$ | 2.553 | -0.363 |
| 15 | rs8041227 | 31538542 | 15q13 | Between LOC283710 and KLF13 | $\mathbf{3.96 \times 10^{-4}}$ | 0.7097 | -0.053 |
| 21 | rs17004598 | 45078556 | 21q22 | HSF2BP | $7.25 \times 10^{-4}$ | 3.059 | -0.493 |

Bolded loci reach genome-wide significance in the combined analysis.
Difference in OR: the difference between the odds ratio of the unadjusted association and the association with atopy adjustment.

Using an independently ascertained cohort that did not overlap with the first EoE GWAS, there was strong replication of disease linkage with 5q22 (rs6594499, Fishers combined p=1.9×10$^{-16}$, Table 8). In Table 8, the results of the previous genome-wide association study of EoE (Rothenberg, M. E. et al. *Nat Genet* 42:289-91 (2010)) was combined with the association of the same variants in the current study using the Fisher's method to combined p values. Subjects included in both studies were removed from the present study before the p value was calculated.

Figure 4A:
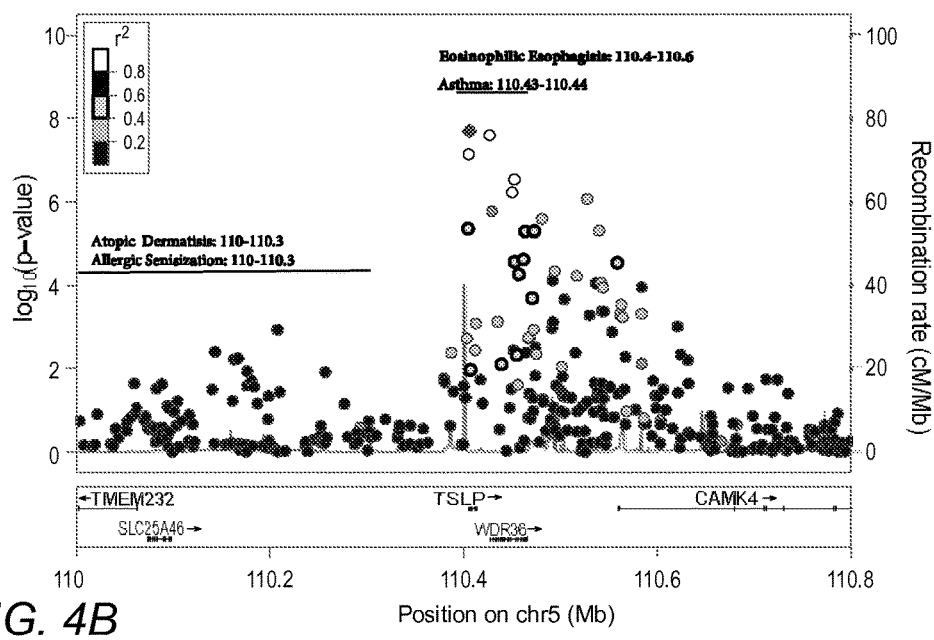
FIG. 4A. Association of genetic variants with EoE in the context of association intervals from related diseases; p-values ($-\log_{10}$)
Figure 4B:
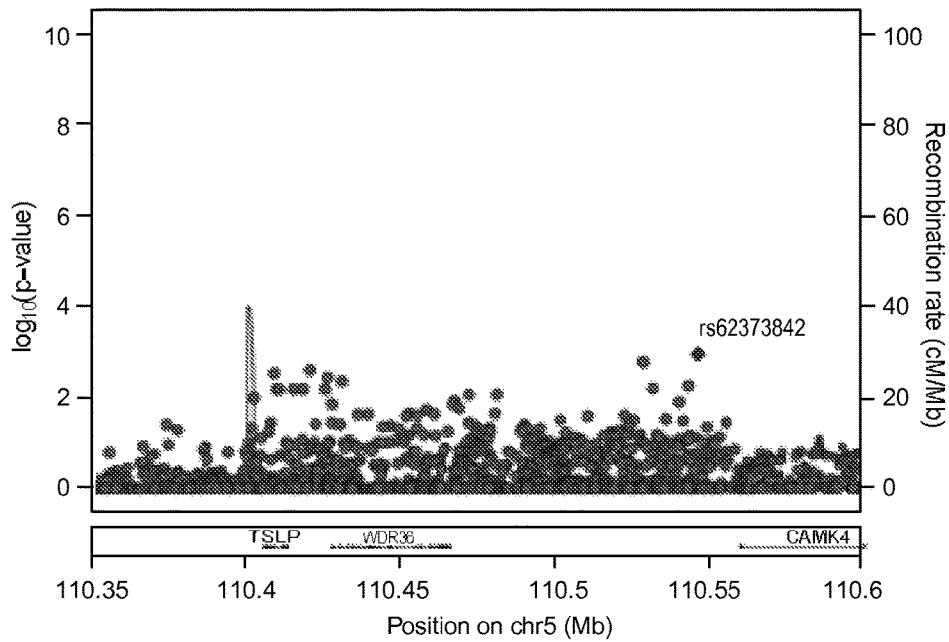
FIG. 4B. Association with EoE adjusted for rs1438672; p-values ($-\log_{10}$) of the genetic association analysis are plotted as a function of genomic positions of each imputed variant (MAF>0.01) on chromosome 5 (Chr 5) adjusting the genotype of rs1438672. Genes in the region are shown. After adjusting for any of the most highly associated variants in the region, a group of variants between TSLP and WDR36 demonstrate residual association p<0.05, suggesting a second genetic effect in the region. The linkage disequilibrium (LD) values ($r^2$) between the lead SNP rs1438672 and the other SNPs are indicated. The solid lines indicate the recombination rates in cM per Mb using HapMap controls.
Figure 5:
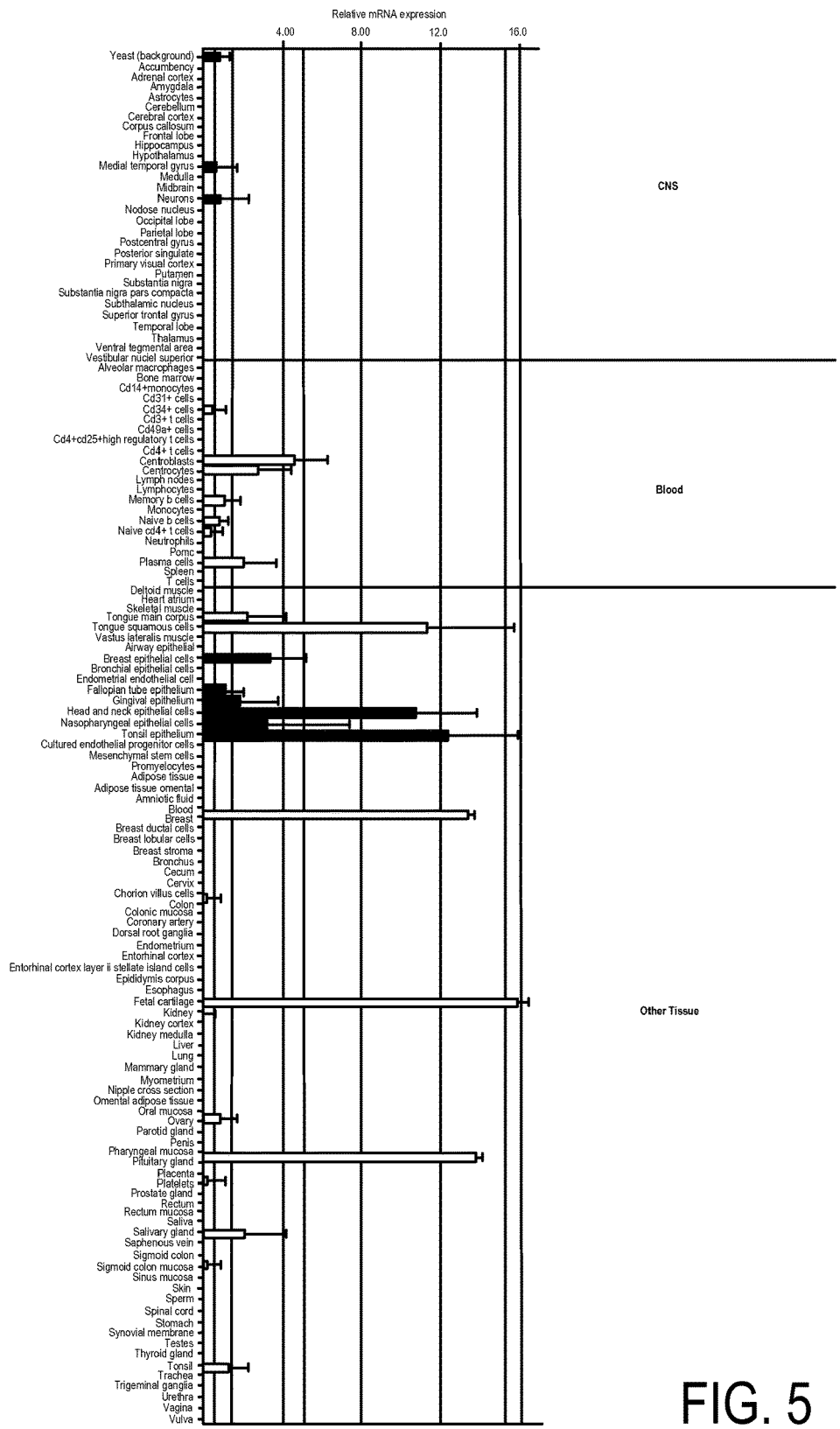
FIG. 5. Expression of CAPN14 (data collected from www <dot> biogps <dot> org). The expression is grouped by tissue source, as indicated on the figure.

After imputing the region to account for all common genetic variation (MAF>1%), the most significant association with the development of EoE was found to be downstream of TSLP and WDR36 at rs1438672 (FIG. 1C) with 12 variants having a p<10$^{-2}$ after adjusting for the most significant variant. In contrast to the EoE susceptibility locus that spanned the TSLP and WDR36 (WD repeat domain 36) genes (FIG. 4), 5q22 variants associated with allergic sensitization (Bonnelykke, K. et al. *Nat Genet* 45:902-6 (2013); Hinds, D. A. et al. *Nat Genet* 45:907-11 (2013); Ramasamy, A. et al. *J Allergy Clin Immunol* 128:996-1005 (2011)), atopic dermatitis (Tang, H. Y. et al. *PLoS One* 7:e35334 (2012); Hirota, T. et al. *Nat Genet* 44:1222-6 (2012)), and allergic rhinitis (Ramasamy, A. et al. *J Allergy Clin Immunol* 128:996-1005 (2011); Iijima, H. et al. *Allergol Int* 62:123-30 (2013)) have all been shown to be upstream of the TSLP gene and the reported association of this locus with asthma (Iijima, H. et al. *Allergol Int* 62:123-30 (2013)) is more limited than the association seen in EoE (FIG. 4). These collective findings indicate that different genetic etiologies are driving the associations at this locus.

TABLE 8

Meta-analysis of the association of SNPs at 5q22.

| SNP | Position | EoE Genome-wide study p value 2009 | EoE Genome-wide study p value 2014 | Combined p value |
|---|---|---|---|---|
| rs3806932 | 110,433,574 | 3.1 × 10$^{-9}$ | 7.2 × 10$^{-8}$ | 2.3 × 10$^{-16}$ |
| rs7723819 | 110,455,246 | 7.6 × 10$^{-9}$ | 2.5 × 10$^{-8}$ | 1.9 × 10$^{-16}$ |
| rs10051830 | 110,480,744 | 2.3 × 10$^{-8}$ | 2.9 × 10$^{-7}$ | 6.6 × 10$^{-16}$ |

Position: build 37 map position of the SNP;
Chr: chromosome and cytogenetic band;
SNP: rs ID of variant.

Variants at 1p13, 5q23, 10p12, 11q13, 11q14, and 21q22 demonstrated suggestive genetic association with EoE risk (p<10$^{-7}$) (Tables 2-3, FIGS. 1 and 7). After establishing statistical associations between genetic variants at these loci and EoE risk, fine mapping studies were performed starting with genotype imputation of common variants (MAF>0.01) that were not captured in the combined GWAS dataset (FIGS. 1 and 4). The 11q13 association was identified in asthma (Ferreira, M. A. et al. *Lancet* 378:1006-14 (2011); Lederer, D. et al. *Am J Hum Genet* 90:119-24 (2012)), atopic dermatitis (Hirota, T. et al. *Nat Genet* 44:1222-6 (2012); Esparza-Gordillo, J. et al. *Nat Genet* 41:596-601 (2009); Greisenegger, E. K. et al. *Eur J Dermatol* 23:142-5 (2013); Paternoster, L. et al. *Nat Genet* 44:187-92 (2012)), inflammatory bowel disease (Barrett, J. C. et al. *Nat Genet* 40:955-62 (2008)), allergic rhinitis (Ramasamy, A. et al. *J Allergy Clin Immunol* 128:996-1005 (2011)), and sensitization to grass (Ramasamy, A. et al. *J Allergy Clin Immunol* 128:996-1005 (2011)). The EoE-associated variants at 11q13 were found to be between C11orf30 (chromosome 11 open reading frame 30) and LRRC32 (the leucine-rich repeat containing 32, also known as GARP). LRRC32 has a role in latent transforming growth factor beta (TGF-β) surface expression (Barrett, J. C. et al. *Nat Genet* 40:955-62 (2008)), and LRRC32 mRNA is highly expressed in activated forkhead box P3 (FOXP3)' T regulatory cells. It is notable that TGF-β and FOXP3' T regulatory cells have been implicated in EoE (Fuentebella, J. et al. *J Pediatr Gastroenterol Nutr* 51:283-9 (2010); Stuck, M. C. et al. *Allergy* 66:705-7 (2011); Tantibhaedhyangkul, U. et al. *Ann Clin Lab Sci* 39:99-107 (2009); Zhu, X. et al. *Am J Physiol Gastrointest Liver Physiol* 297:G550-8 (2009); Frischmeyer-Guerrerio, P. A. et al. *Sci Transl Med* 5:195ra94 (2013)).

Figure 6A:
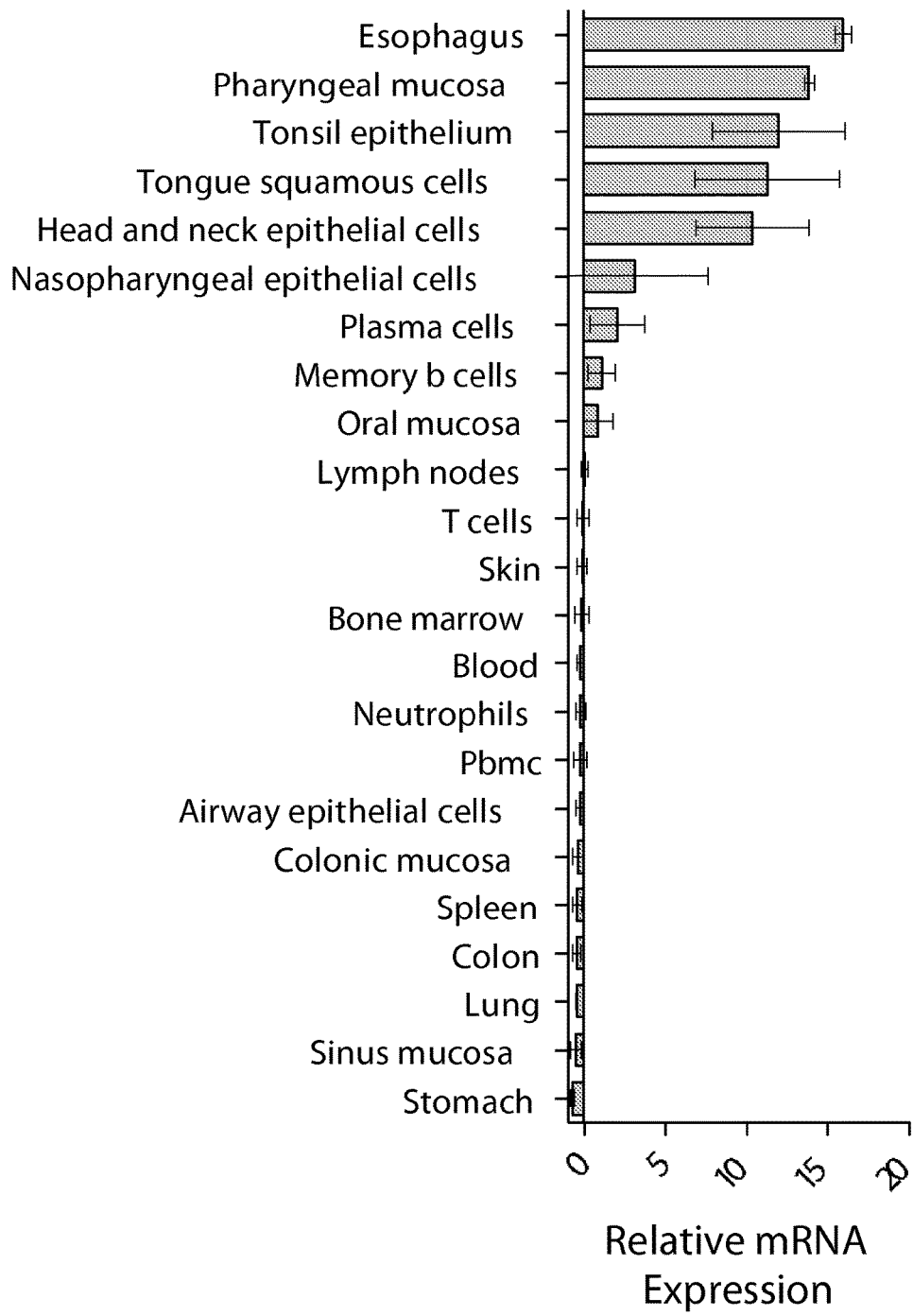
FIG. 6A. Barcode Z-score relative microarray expression of CAPN14 in various human tissue samples based on biogps <dot> org. Representative data are from multiple cellular subtypes.
Figure 6B:
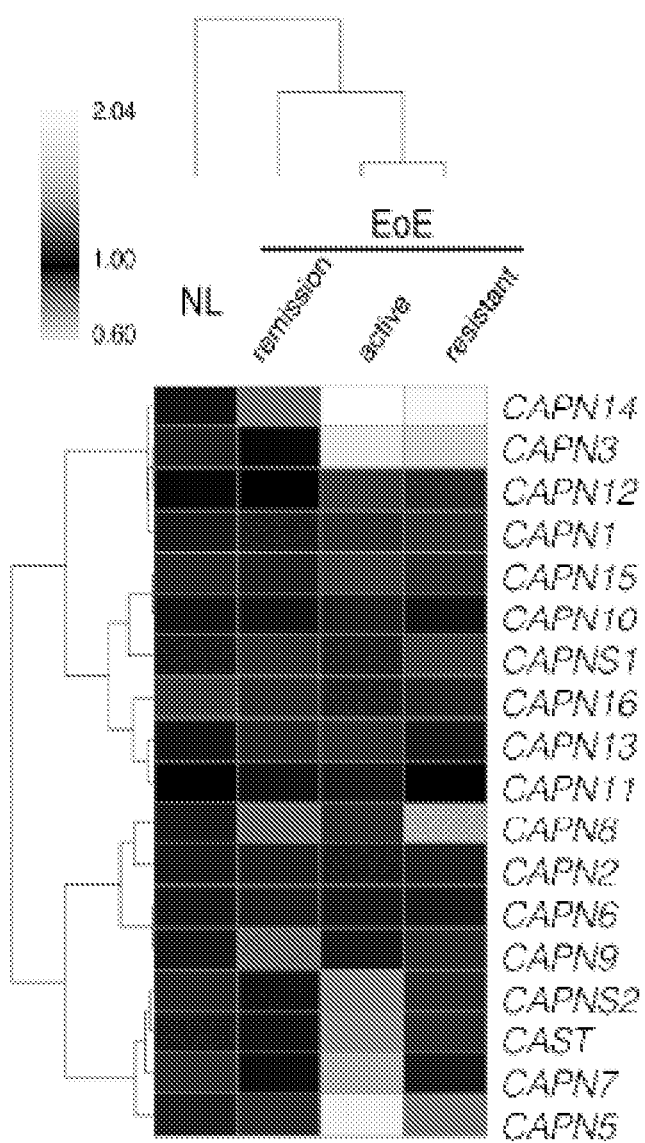
FIG. 6B. Microarray expression heat map of esophageal biopsies from normal controls (NL, n=14), therapy-responsive EoE patients (EoE remission, n=18), active EoE patients (EoE active, n=18), and therapy-non-responsive EoE patients (EoE resistant, n=19).
Figure 7A:
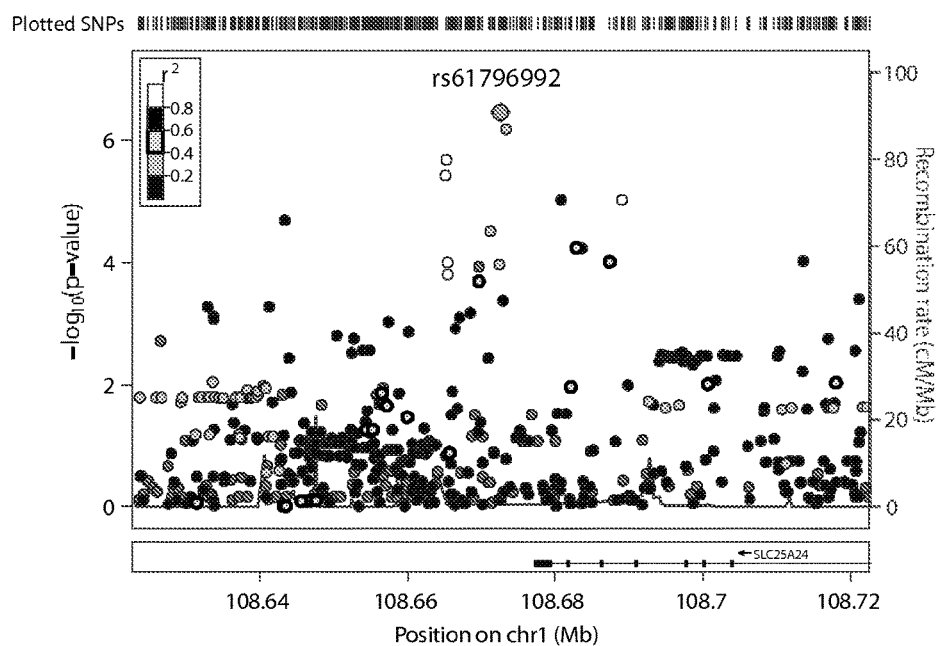
FIG. 7. Fine mapping of loci associated (replicated and $5\times10^{-8}<p<10^{-6}$) with EoE risk. P values ($-\log_{10}$) of the genetic association analysis of imputed variants on the y-axis are plotted as a function of genomic positions of each genotyped and imputed SNPs (MAF>0.05). Genes in the region are shown. The LD values ($r^2$) between the lead SNP and the other SNPs as assessed in the March 2012 release of the 1,000 genomes project are indicated in different shades. The solid lines indicate the recombination rates in cM per Mb using HapMap controls. 7A. Fine mapping for 1q13. 7B. Fine mapping for 5q23. 7C. Fine mapping for 10p12. 7D. Fine mapping for 11q13. 7E. Fine mapping for 11q14. 7F. Fine mapping for 21q22.
Figure 7B:
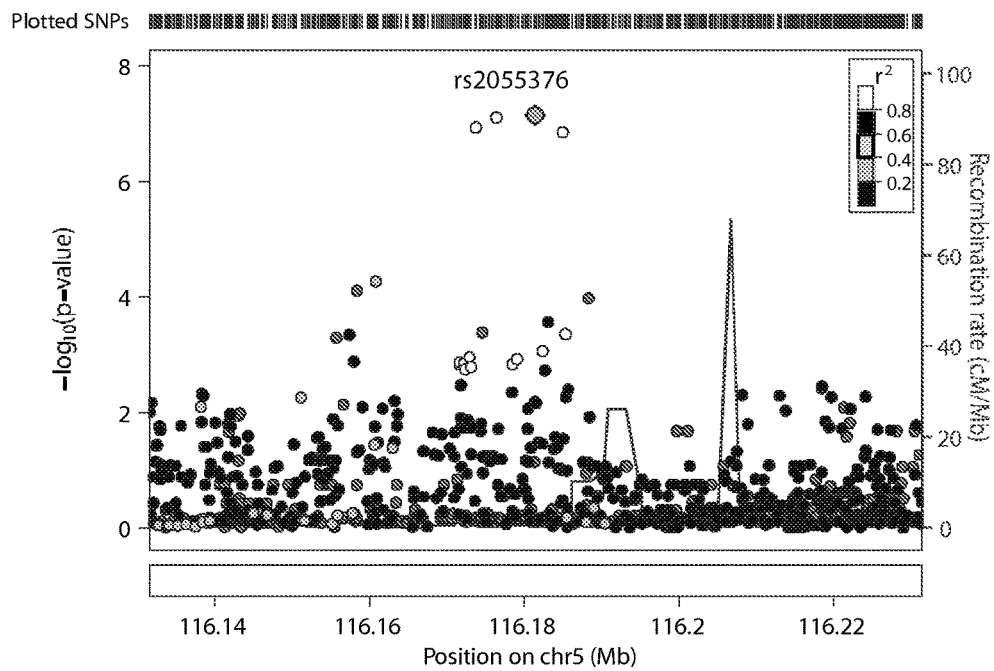
Figure 7C:
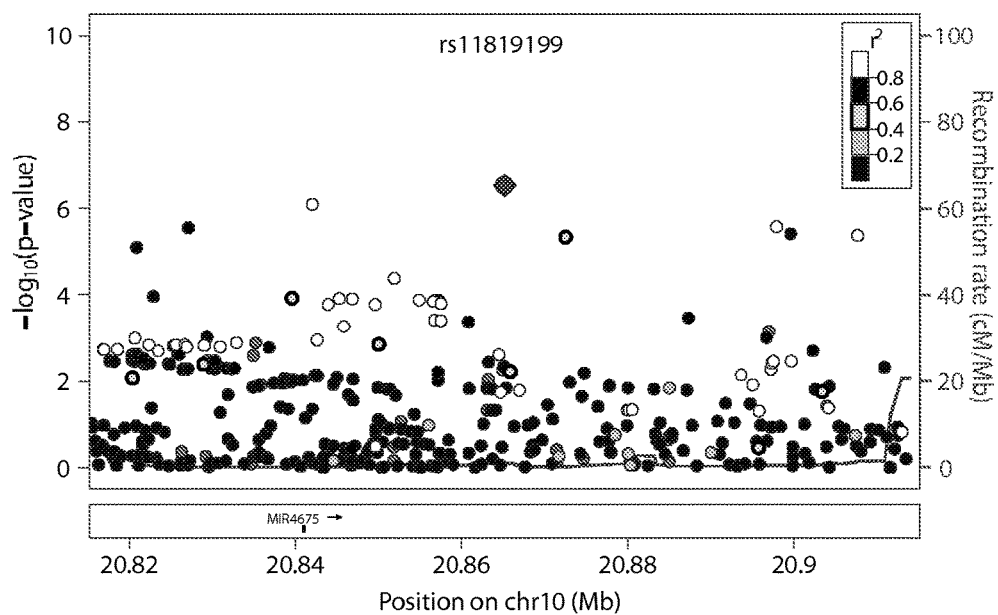
Figure 7D:
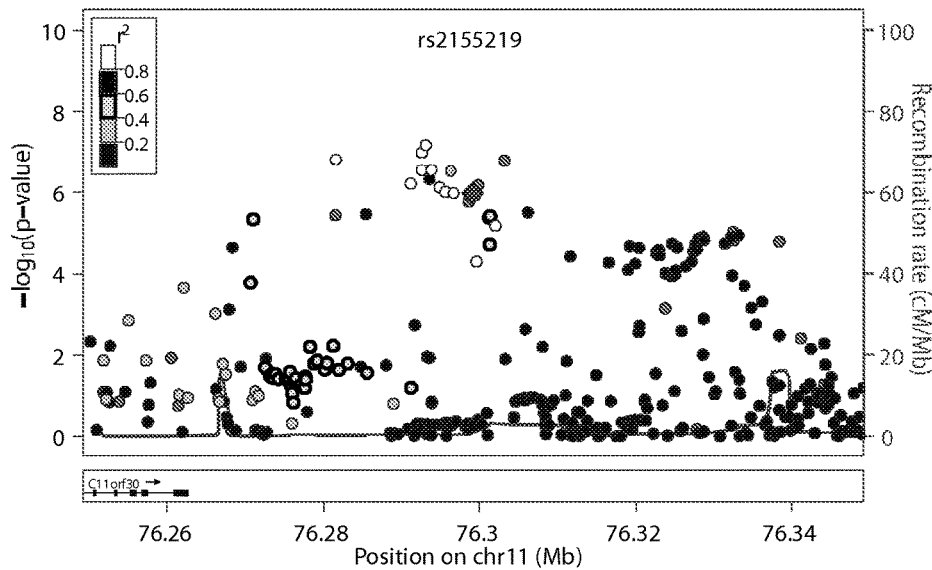
Figure 7E:
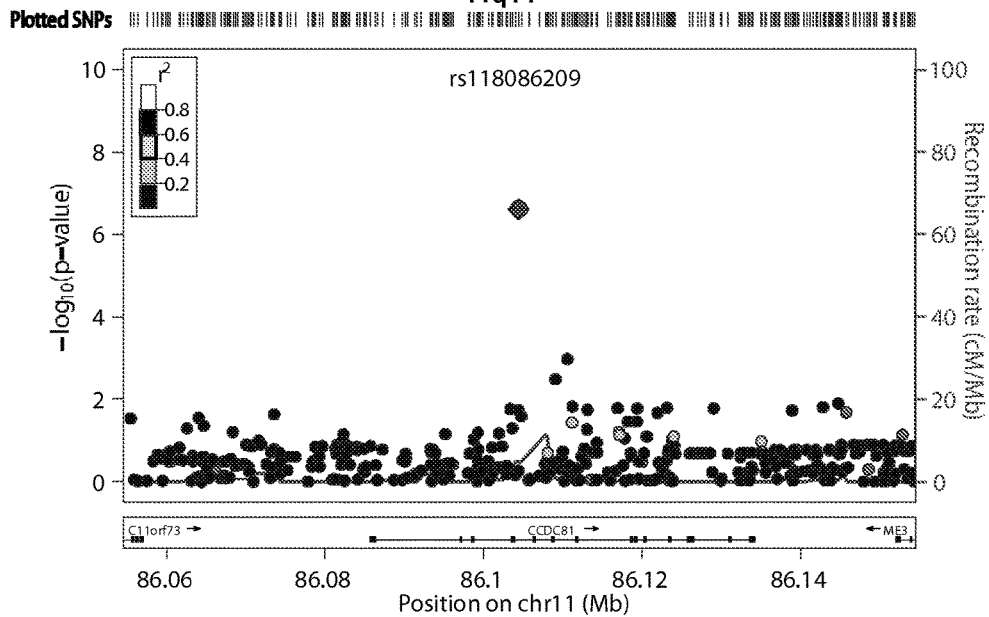
Figure 7F:
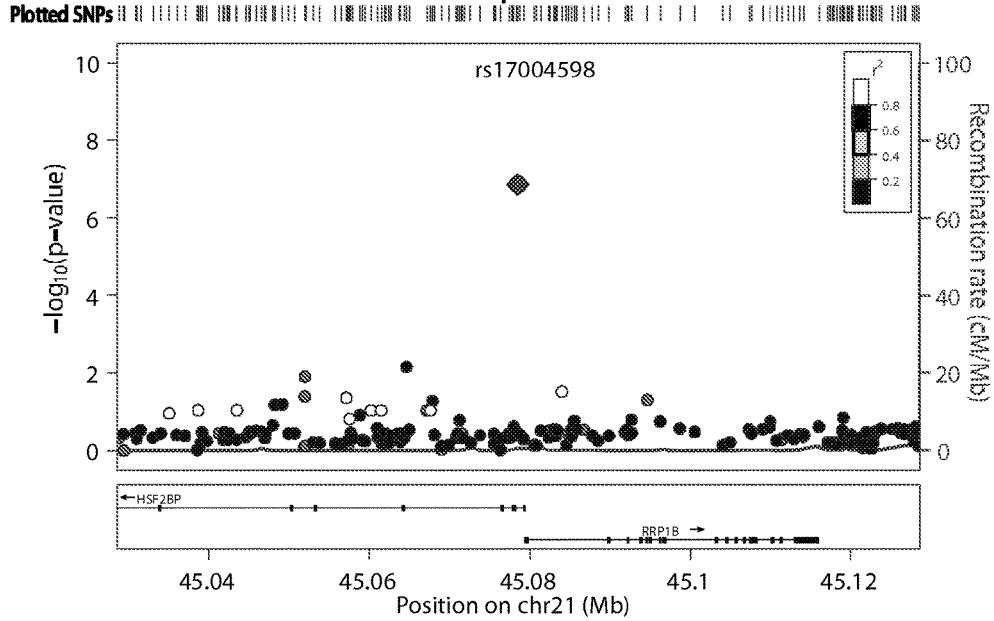

CAPN14 encodes for calpain 14, a calcium-activated cysteine protease. A survey of 130 tissues revealed that CAPN14 was most highly expressed in the esophagus (FIGS. 6A and 7). When the expression of the calpain family members was assessed in biopsies from subjects with and without EoE, a distinct pattern was found for control, treated EoE, and untreated EoE subjects; notably CAPN14 was dynamically expressed as a function of disease activity (FIG. 6B). CAPN14 showed the largest upregulation compared with all members of the CAPN family (FIG. 6B), but three of the other fifteen family members were also dysregulated in EoE esophageal biopsies, namely CAPN3, CAPN5, and CAST (calpastatin) (FIG. 6B). CAST is a calpain inhibitor and was downregulated (29%, p<10$^{-4}$). A >2-fold increase in CAPN14 expression was found in the esophageal biopsies of patients with active EoE (FIG. 6C). Furthermore, IL-13 stimulation of primary esophageal epithelial cells and an esophageal epithelial cell line grown at the air-liquid interface with IL-13 resulted in a 4-fold and >100-fold increase in CAPN14 expression, respectively. (FIGS. 6D and 6G). Patients with the risk haplotype expressed 30% lower CAPN14 mRNA than those without the risk allele (p<10$^{-2}$) (FIG. 6E).

To identify the genomic mechanisms that drive the statistical association of EoE risk at 2p23, chromatin immunoprecipitation sequencing (ChIP-seq) was performed on chromatin from esophageal epithelial cells treated with IL-13. Of the six SNPs most highly associated at the CAPN14 locus after imputation, two (rs76562819 and rs75960361) were located in likely regulatory regions, on the basis of the IL-13-induced H3K27Ac ChIP-seq marks of esophageal epithelial cells as well as publically available ENCODE functional genomics data (including histone marks, DNaseI hypersensitivity data, and ChIP-seq data) (Maher, B. *Nature* 489:46-8 (2012); Ecker, J. R. et al. *Nature* 489:52-5 (2012); Skipper, M. et al. *Nature* 489:45 (2012)) (FIG. 6H).

The rs76562819 SNP is located proximal to the 5' of the CAPN14 transcription start site (FIG. 6H), lies within a region of elevated H3K4Me1 histone marks in multiple cells lines, and intersects with open chromatin regions in thirty-four cell types on the basis of DNaseI hypersensitivity site mapping data. An electrophoretic mobility shift assay (EMSA) was subsequently performed using a capture probe from this region; this study found that the risk allele (rs7462819) preferentially bound to a nuclear protein complex compared to the non-risk allele (FIG. 6I).

Figure 8B:
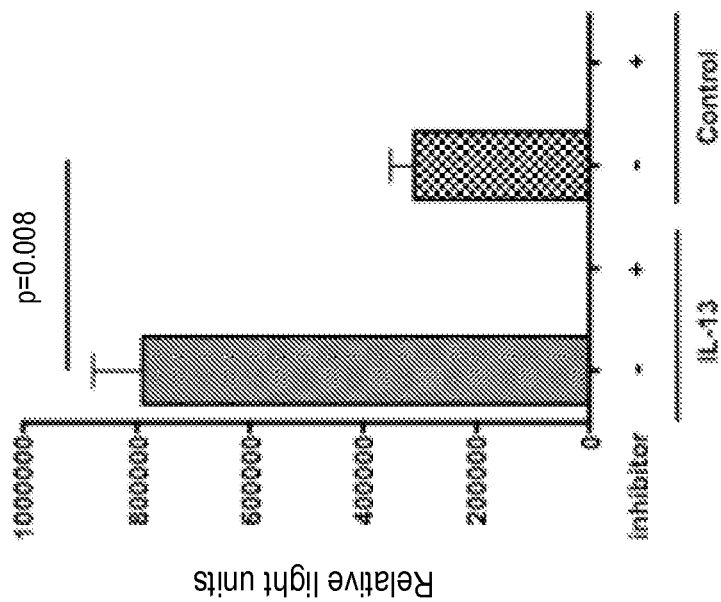
FIG. 8B. Calpain activity assay in EPC2 cells with or without IL-13 stimulation for 48 hours in the presence or absence of the calpain inhibitor acetyl-calpastatin. Error bars represent s.e.m.
Figure 8A:
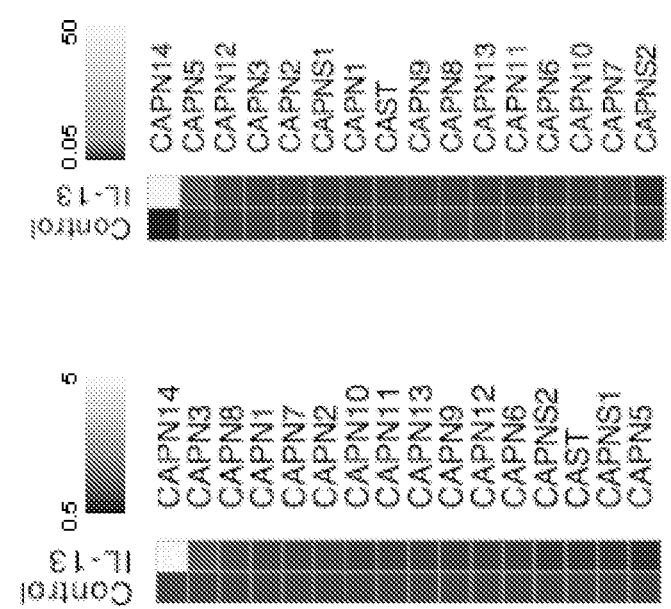
FIG. 8A. Heat map of microarray expression of the calpain family in primary esophageal epithelial cell culture (left) and in EPC2 air-liquid interface cultures (right).

CAPN14 was the only CAPN family member to be upregulated as measured by microarray and RNA sequencing (RNA-seq) in either primary epithelial cells from esophageal biopsies and in the organotypic culture after treatment with IL-13 (FIG. 8A). These results were consistent with preliminary findings in corneal and conjunctival epithelial cells (Ueta, M. et al. *Br J Ophthalmol* 94, 1239-43 (2010); Ueta, M. et al. *Jpn J Ophthalmol* 55:405-10 (2011)).

IL-13 increased calpain activity in esophageal epithelial cells treated with IL-13, and this activity was inhibited by calpastatin (FIG. 8B).

To provide insight into the molecular mechanisms underlying each of the ten replicated associations, proximal (cis-acting) expression quantitative trait loci (eQTLs) were searched using gene expression data obtained from six cell types or tissues (white blood cells (WBCs), lymphoblastoid cell lines (LCLs), whole blood, adipose tissue, B cells and monocytes). At two of the ten most highly associated EoE-risk loci, the sentinel SNP was associated ($p<10^{-3}$) with the expression of one or more nearby genes. In particular, the most highly associated variants at 1p13 and 8p23 were strongly associated with the expression of the nearest genes SLC25A24 (solute carrier family 25 (mitochondrial carrier; phosphate carrier), member 24; $p=1.25\times10^{-9}$) and XKR6 ($p=1.02\times10^{-7}$) (Table 9), suggesting that these variants might affect disease risk through the modulation of gene expression. From internal expression databases, this group has previously reported that TSLP expression is upregulated in the biopsies of EoE patients in an allele dependent manner and in esophageal epithelial cell lines treated with polyinosinic:polycytidylic acid (Rothenberg, M. E. et al. *Nat Genet* 42:289-91 (2010); Sherrill, J. D. et al. *J Allergy Clin Immunol* 126:160-5 e3 (2010)).

TABLE 9

Expression quantitative trait loci (eQTL) analysis of top EoE risk-variants in a public database with expression from peripheral blood mononuclear cells.

| CHR | SNP | SNP position | Probe | Z-score | Gene name | P-value |
|---|---|---|---|---|---|---|
| 1 | rs2000260 | 108474928 | 7510681 | 6.07 | SLC25A24 | 1.25E−09 |
| 8 | rs2898261 | 10995949 | 4730672 | 5.32 | XKR6 | 1.02E−07 |

Chr: chromosome and cytogenetic band;
SNP: rs ID of variant;
SNP Position: build 37 map position of the SNP.

Figure 9:
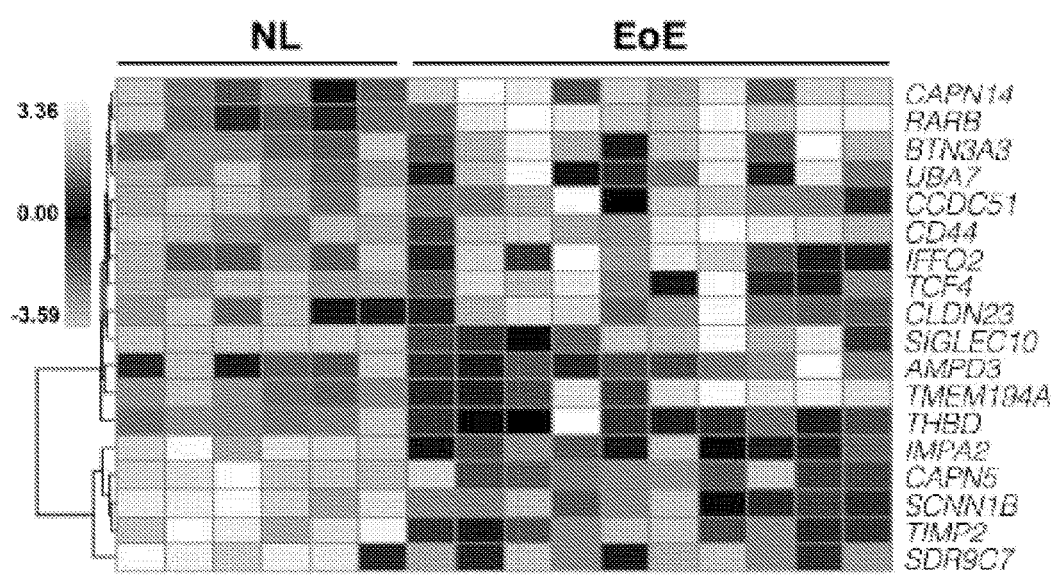
FIG. 9. Genes at EoE risk loci with differential expression in biopsies from EoE patients compared to controls. Genes within 25 kb of the 768 genetic variants associated with EoE (combined $p<10^{-4}$) were used in this analysis of RNA-seq data. The expression of 208 genes was assessed. Normalized fold-change is shown for all genes (with 2-fold average change and corrected p<0.05). NL, normal controls.
Figure 10:
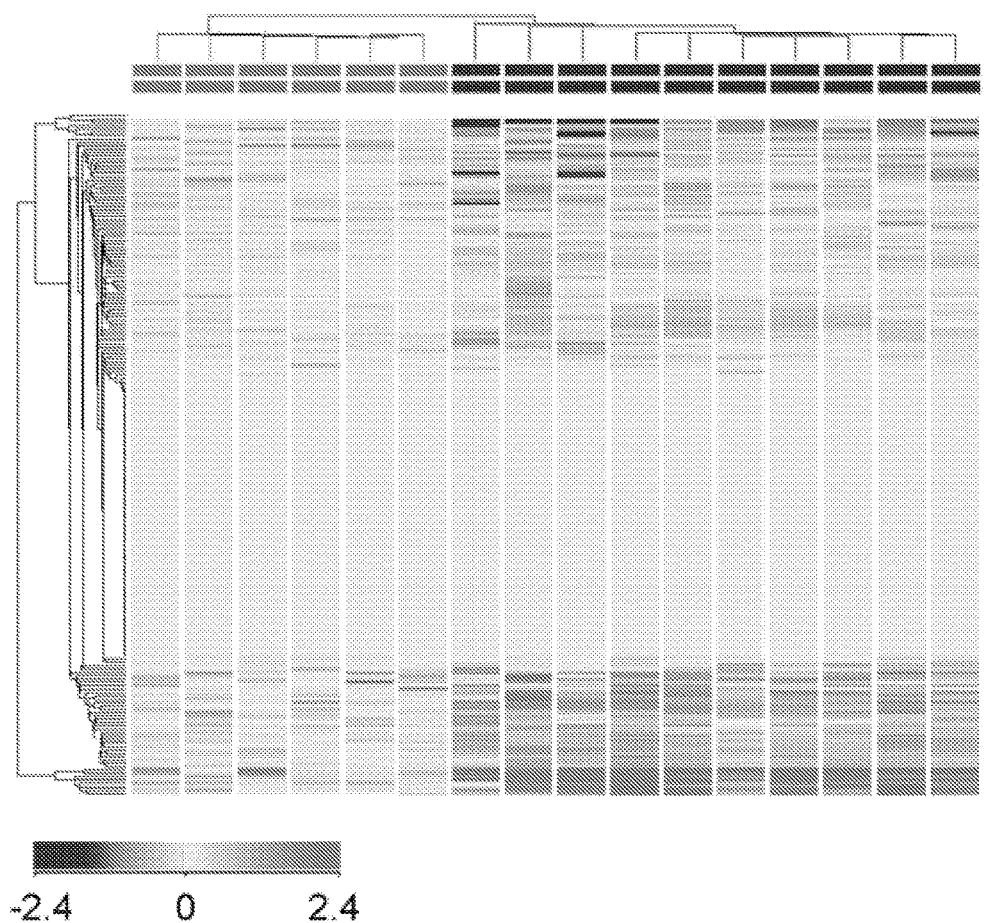
FIG. 10. Expression of genes near EoE-associated genetic variants ($p<10^{-4}$) in the esophageal biopsies of EoE patients vs controls. In this dataset, 98 of the 215 have an average of ≥2 FPKMs. The differences in expression were sufficient to segregate EoE cases from controls. The 8 transcripts with differences in expression greater than 2-fold can be found in FIG. 9. Subjects with EoE are noted with black bars, and subjects without EoE are indicated in grey. All expression is normalized to the average expression in esophageal biopsies without EoE.
Figure 11:
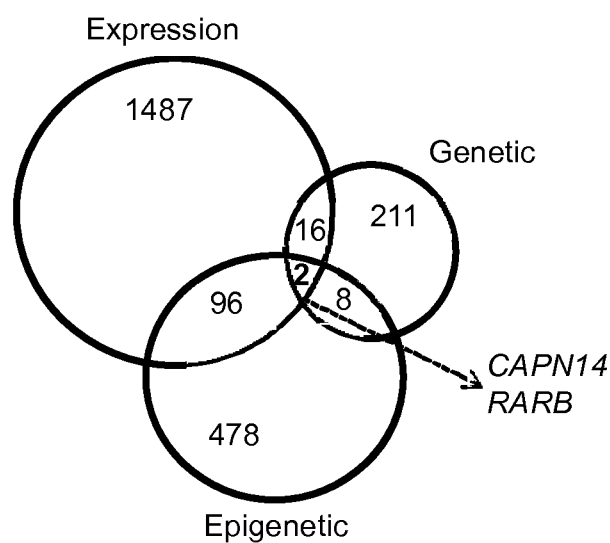
FIG. 11. Two genes including CAPN14 are identified in EoE genetic, expression, and epigenetic analyses. Overlap from analyses of genes were assessed within 25 kb of genetic variant with $p<10^{-4}$, genes with increased H3K27Ac after 6 hour exposure to IL-13 (p<0.01, M<−1 at 5 kb from TSS), and genes with increased esophageal expression in EoE (2-fold increase in expression in esophageal biopsy in EoE compared to control, corrected p<0.05).

The RNA-seq expression of all genes within 25 kb of variants with combined $p<10^{-4}$ was measured. Of these 208 genes, 48% were expressed in the esophagus at appreciable levels; this represented an enrichment compared with the expression of the whole genome in the esophagus ($p<10^{-4}$). Furthermore, the differential expression of these genes was sufficient to segregate EoE cases from controls, and 8% of the genes near the most highly associated EoE risk loci were differentially expressed (>2-fold average change, Bonferroni adjusted $p<5\times10^{-2}$) in EoE patients vs. control biopsies (FIGS. 9 and 10). Therefore, these data demonstrate a concentration of EoE susceptibility loci in the neighborhood of genes expressed and/or dysregulated in the esophagus of diseased patients, suggesting a local functional role for the implicated gene. In addition, this study aimed to determine whether any of the differentially expressed GWAS associations had increased H3K27Ac marks in epithelial cells after IL-13 treatment. Notably, CAPN14 was one of two genes with these IL-13-responsive characteristics (FIG. 11). This analysis further underscores the centrality of CAPN14 in the etiology of EoE. These data are consistent with the mechanistic model in which CAPN14 is dynamically expressed in the esophagus in response to inflammatory stimuli, a regulatory mechanism disrupted by the decreased expression associated with the risk haplotype (FIG. 12).

The previous genome-wide study of EoE did not assess the most significant variant in CAPN14 but did identify suggestive association ($p<10^{-4}$) from variants in the region (Rothenberg, M. E. et al. *Nat Genet* 42:289-91 (2010)). With additional EoE cases and controls, the current study was better powered to identify statistically significant association of genetics variants with the development of EoE. Several recent GWAS reported 22 loci associated with allergic sensitization (Bonnelykke, K. et al. *Nat Genet* 45:902-6 (2013); Hinds, D. A. et al. *Nat Genet* 45:907-11 (2013)). EoE association was found at 9 of these 22 loci (Table 10) using a cut-off of $p<5\times10^{-2}$, underscoring the key role of atopy in EoE; 8 of these SNPs were associated with comparable disease risk effects. The atopic sensitization loci with the greatest association with EoE were at CLEC16A, LRRC32, LPP (C-type lectin domain family 16, member A, Leucine rich repeat containing 32, LIM domain containing preferred translocation partner in lipoma), and TSLP/WDR36 (FIGS. 1 and 12). However, of the ten replicated loci that were linked with EoE in this study, only two overlapped with the 22 allergic sensitization loci, highlighting that non-atopy related processes can be operational.

TABLE 10

EoE genetic linkage with allergic sensitization markers[+].

| Chr | Marker | Position | Gene | Odds Ratio AS | p-value | Odds Ratio EoE |
|---|---|---|---|---|---|---|
| 1 | rs2056417 | 10581658 | PEX14 | 1.07 | 0.26 | 0.927 |
| 2* | rs10174949 | 8442248 | ID2 | 1.07 | 0.32 | 0.95 |
| 2 | rs10189629 | 102879464 | IL1RL2/IL1RL1 | 1.16 | 0.84 | 1.02 |
| 2* | rs10497813 | 198914072 | PLCL1 | 0.92 | 0.031 | 0.888 |
| 3* | rs9860547 | 188128979 | LPP | 1.08 | $5.0 \times 10^{-7}$ | 1.32 |
| 4* | rs2101521 | 38811551 | TLR1/TLR6 | 1.12 | 0.43 | 0.948 |
| 4 | rs17388568 | 123329362 | ADAD1 | 1.08 | 0.11 | 1.11 |
| 5 | rs7720838 | 40486896 | PTGER4 | 1.08 | 0.91 | 1 |
| 5* | rs1438673 | 110467499 | WDR36/CAMK4 | 0.89 | $5.1 \times 10^{-11}$ | 0.685 |
| 6 | rs9266772 | 31352113 | HLA-C/MICA | 1.11 | 0.28 | 1.086 |
| 6 | rs6906021 | 32626311 | HLA-DQA1/HLA-DQB1 | 1.1 | 0.26 | 1.08 |
| 8 | rs6473223 | 81268155 | TPD52/ZBTB10 | 1.07 | 0.00019 | 1.26 |
| 9 | rs7032572 | 6172380 | RANBP6/IL33 | 1.12 | 0.048 | 1.17 |
| 10* | rs962993 | 9053132 | GATA3 | 0.93 | 0.019 | 0.877 |
| 11 | rs2155219 | 76299194 | C11orf30/LRRC32 | 0.9 | $1.1 \times 10^{-6}$ | 0.759 |
| 11 | rs10893845 | 128186882 | ETS1 | 1.06 | 0.73 | 0.979 |
| 14* | rs1998359 | 38077148 | FOXA1/TTC6 | 1.08 | 0.66 | 1.03 |
| 15* | rs17228058 | 67450305 | SMAD3 | 1.08 | 0.0032 | 1.2 |
| 16* | rs2107357 | 27410829 | IL4R/IL21R | 1.09 | 0.53 | 0.948 |
| 17* | rs9303280 | 38074031 | GSDMB | 1.07 | 0.51 | 0.964 |

TABLE 10-continued

EoE genetic linkage with allergic sensitization markers[†].

| Chr | Marker | Position | Gene | Odds Ratio AS | p-value | Odds Ratio EoE |
|---|---|---|---|---|---|---|
| 16 | rs7203459 | 11230703 | CLEC16A | 0.93 | $4.6 \times 10^{-5}$ | 0.731 |
| 20 | rs6021270 | 50141264 | NFATC2 | 1.16 | 0.57 | 1.07 |

[†]Association of variants previously reported as genome-wide significant in two GWAS of allergic sensitization (AS) (Bonnelykke, K. et al. *Nat Genet* 45: 902-6 (2013); Hinds, D.A. et al. *Nat Genet* 45: 907-11 (2013)).
An asterisk by the chromosome indicates that the variant was imputed from the EoE GWAS.
The odds ratios are given for the allele with the smallest frequency (the minor allele) in the EoE analysis.

In conclusion, herein the number of established susceptibility loci for EoE has been increased from one to four; this study presents compelling evidence for six other loci. These data substantiate a mechanism to explain the tissue specific manifestations of this prototypic allergic disease. In particular, this study provides evidence for the interaction of shared genetic and molecular pathways between general atopy risk factors (e.g. TSLP/WDR36, LRR32, IL-33, LPP) and EoE disease specific elements, most notably genetic risk factors present at 2p23 where CAPN14 is located. Consistent with this model, the CAPN14 gene is located in a baseline epigenetic hotspot that is modified by IL-13, and CAPN14 is specifically expressed in esophageal epithelium and is dynamically upregulated as a function of disease activity and genetic haplotype and after exposure of epithelial cells to IL-13. Mutations in CAPN3, whose gene product is specifically expressed in skeletal muscle, have been associated with susceptibility to another tissue specific eosinophilic disorder (eosinophilic myositis) (Krahn, M. et al. *Clin Genet* 80:398-402 (2011); Krahn, M. et al. *Ann Neurol* 59:905-11 (2006); Bartoli, M. et al. *Clin Genet* 81:99-101 (2012); Brown, R. H., Jr. and Amato, A. *Ann Neurol* 59:875-7 (2006); Amato, A. A. *Neurology* 70:730-1 (2008); Oflazer, P. S. et al. *Neuromuscul Disord* 19:261-3 (2009)). CAPN14 belongs to the classical calpain sub-family that comprises one of the major proteolytic systems that mediate protein cleavage (in addition to the proteasome, lysosome, and caspase systems) (Sorimachi, H. et al. *Proc Jpn Acad Ser B Phys Biol Sci* 87:287-327 (2011)). Known substrates for classical calpains include structural proteins, signaling molecules, transcription factors (Arnandis, T. et al. *Biochem J* (Epub ahead of print) (2014): Wang, Y. and Zhang, Y. *Cell Rep* 6:278-84 (2014)), and inflammatory mediators that are germane for allergic responses, such as STAT-6 (signal transducer and activator of transcription 6) and IL-33 (Meephansan, J. et al. *J Invest Dermatol* 132:2593-600 (2012); Hayakawa, M. et al. *Biochem Biophys Res Commun* 387:218-22 (2009)), the latter of which shows some linkage with EoE (FIG. 11 and Table 10). On the basis of the collective data, these results link the interplay of allergic sensitization with an EoE-specific IL-13-inducible esophageal response involving CAPN14.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of diagnosing and treating eosinophilic esophagitis (EoE) in a patient, the method comprising
    obtaining or receiving a biological sample from the patient;
    detecting the presence of one or more genetic variants selected from the group consisting of rs77569859 (CAPN14), rs2898261 (XKR6), and rs8041227 (located at 15q13 between LOC283710 and KLF13) in the sample;
    assigning the patient into a risk group selected from low, moderate, and high, based upon the detection of the one or more genetic variants as follows:
        rs77569859 (CAPN14) GG high, GA moderate, AA low,
        rs2898261 (XKR6) CC high, AC moderate, CC low, and
        rs8041227 (15q13) GG high, AG moderate, AA low,
    diagnosing the patient assigned to the high or moderate group with EoE;
    administering an EoE therapy to the diagnosed patient.

2. The method of claim 1, wherein the EoE therapy comprises administering a steroid.

3. The method of claim 1, wherein the EoE therapy comprises administering proton pump inhibitor.

4. The method of claim 1, wherein the EoE therapy comprises administering a topical glucocorticoid.

5. The method of claim 1, wherein the EoE therapy comprises administering an inhibitor of eosinophil recruitment, survival, or activation.

6. The method of claim 1, wherein the presence of the one or more genetic variants is determined by a method comprising extracting DNA from the biological sample and analyzing the DNA to determine the patient's genotype at the at least one genetic variant.

7. The method of claim 6, wherein the patient's genotype is received directly from equipment used in determining the patient's genotype.

8. The method of claim 7, wherein the genotyping platform utilizes a 5' nuclease assay for amplifying and detecting specific genetic variants.

9. The method of claim 6, wherein the DNA is analyzed using a polymerase chain reaction based genotyping platform.

10. The method of claim 1, wherein the biological sample is selected from a blood sample, a saliva sample, and a buccal swab.

* * * * *